United States Patent
Sunkeri et al.

(10) Patent No.: US 11,420,045 B2
(45) Date of Patent: Aug. 23, 2022

(54) LEADS HAVING SIDEWALL OPENINGS, AND ASSOCIATED SYSTEMS AND METHODS

(71) Applicant: Nevro Corp., Redwood City, CA (US)

(72) Inventors: Pankaj Sunkeri, Belmont, CA (US); Apratim N. Dixit, Menlo Park, WA (US)

(73) Assignee: Nevro Corp., Redwood City, CA (US)

( * ) Notice: Subject to any disclaimer, the term of this patent is extended or adjusted under 35 U.S.C. 154(b) by 355 days.

(21) Appl. No.: 16/367,873

(22) Filed: Mar. 28, 2019

(65) Prior Publication Data

US 2019/0308010 A1 Oct. 10, 2019

Related U.S. Application Data

(60) Provisional application No. 62/650,111, filed on Mar. 29, 2018.

(51) Int. Cl.
*A61N 1/00* (2006.01)
*A61N 1/05* (2006.01)
*A61N 1/36* (2006.01)
*A61N 1/378* (2006.01)

(52) U.S. Cl.
CPC ......... *A61N 1/0553* (2013.01); *A61N 1/0534* (2013.01); *A61N 1/0558* (2013.01); *A61N 1/36003* (2013.01); *A61N 1/36071* (2013.01); *A61N 1/36171* (2013.01); *A61N 1/3787* (2013.01)

(58) Field of Classification Search
USPC ...................................................... 607/117
See application file for complete search history.

(56) References Cited

U.S. PATENT DOCUMENTS

| | | | |
|---|---|---|---|
| 3,195,540 A | 7/1965 | Waller et al. |
| 3,724,467 A | 4/1973 | Avery et al. |
| 3,774,618 A | 11/1973 | Avery |
| 3,796,221 A | 3/1974 | Hagfors |
| 4,096,866 A | 6/1978 | Fischell |
| 4,136,703 A | 1/1979 | Wittkampf |
| 4,141,365 A | 2/1979 | Fischell et al. |

(Continued)

FOREIGN PATENT DOCUMENTS

| | | |
|---|---|---|
| CN | 101920065 A | 12/2010 |
| EP | 0158316 A2 | 10/1985 |

(Continued)

OTHER PUBLICATIONS

US 6,184,239 B1, 02/2001, Puskas (withdrawn)

(Continued)

*Primary Examiner* — Nicole F Lavert
(74) *Attorney, Agent, or Firm* — Perkins Coie LLP

(57) ABSTRACT

The present technology is generally directed to spinal cord modulation leads having one or more sidewall openings configured for inserting stylets to steer and/or position the leads within a patient and/or with respect to a pulse generator, and associated systems and methods. In some embodiments, sidewall opening is generally positioned in an intermediate portion of the lead and is operatively coupled to a lumen extending distally to a distal end of the lead, and/or proximally to a proximal end of the lead.

52 Claims, 9 Drawing Sheets

(56) References Cited

U.S. PATENT DOCUMENTS

| | | |
|---|---|---|
| 4,282,886 A | 8/1981 | King |
| 4,285,347 A | 8/1981 | Hess |
| 4,328,813 A | 5/1982 | Ray |
| 4,355,224 A | 10/1982 | Mesick et al. |
| 4,374,527 A | 2/1983 | Iversen |
| 4,379,462 A | 4/1983 | Borkan et al. |
| 4,383,532 A | 5/1983 | Dickhudt |
| 4,414,986 A | 11/1983 | Dickhudt et al. |
| 4,422,917 A | 12/1983 | Hayfield |
| 4,432,377 A | 2/1984 | Dickhudt |
| 4,462,401 A | 7/1984 | Burgio |
| 4,462,402 A | 7/1984 | Burgio et al. |
| 4,465,079 A | 8/1984 | Dickhudt |
| 4,466,690 A | 8/1984 | Osypka |
| 4,498,482 A | 2/1985 | Williams |
| 4,515,168 A | 5/1985 | Chester et al. |
| 4,538,624 A | 9/1985 | Tarjan |
| 4,573,448 A | 3/1986 | Kambin |
| 4,573,481 A | 3/1986 | Bullara |
| 4,579,120 A | 4/1986 | MacGregor |
| 4,603,696 A | 8/1986 | Cross, Jr. et al. |
| 4,658,835 A | 4/1987 | Pohndorf |
| 4,683,895 A | 8/1987 | Pohndorf |
| 4,721,551 A | 1/1988 | Byers et al. |
| 4,744,370 A | 5/1988 | Harris |
| 4,744,371 A | 5/1988 | Harris |
| 4,764,132 A | 8/1988 | Stutz, Jr. |
| 4,796,642 A | 1/1989 | Harris |
| 4,830,776 A | 5/1989 | Thompson |
| 4,898,173 A | 2/1990 | Low et al. |
| 4,919,653 A | 4/1990 | Martinez et al. |
| 4,920,979 A | 5/1990 | Bullara |
| 4,926,878 A | 5/1990 | Snedeker |
| 4,934,367 A | 6/1990 | Daglow et al. |
| 4,934,383 A | 6/1990 | Glumac |
| 4,940,065 A | 7/1990 | Tanagho et al. |
| 4,961,434 A | 10/1990 | Stypulkowski |
| 4,979,511 A | 12/1990 | Terry, Jr. |
| 5,000,194 A | 3/1991 | van den Honert et al. |
| 5,007,902 A | 4/1991 | Witt |
| 5,036,862 A | 8/1991 | Pohndorf |
| 5,042,486 A | 8/1991 | Pfeiler et al. |
| 5,046,511 A | 9/1991 | Maurer et al. |
| 5,070,605 A | 12/1991 | Daglow |
| 5,072,458 A | 12/1991 | Suzuki |
| 5,078,140 A | 1/1992 | Kwoh |
| 5,081,990 A | 1/1992 | Deletis |
| 5,121,754 A | 6/1992 | Mullett |
| 5,129,404 A | 7/1992 | Spehr et al. |
| 5,159,926 A | 11/1992 | Ljungstroem |
| 5,179,962 A | 1/1993 | Dutcher et al. |
| 5,190,529 A | 3/1993 | McCrory et al. |
| 5,205,297 A | 4/1993 | Montecalvo et al. |
| 5,211,165 A | 5/1993 | Dumoulin et al. |
| 5,257,636 A | 11/1993 | White |
| 5,265,608 A | 11/1993 | Lee et al. |
| 5,273,053 A | 12/1993 | Pohndorf |
| 5,306,236 A | 4/1994 | Blumenfeld et al. |
| 5,314,458 A | 5/1994 | Najafi et al. |
| 5,325,873 A | 7/1994 | Hirschi et al. |
| 5,351,394 A | 10/1994 | Weinberg |
| 5,351,687 A | 10/1994 | Kroll et al. |
| 5,351,697 A | 10/1994 | Cheney |
| 5,354,326 A | 10/1994 | Comben et al. |
| 5,360,441 A | 11/1994 | Otten |
| 5,366,489 A | 11/1994 | Burgio et al. |
| 5,375,596 A | 12/1994 | Twiss |
| 5,392,791 A | 2/1995 | Nyman et al. |
| 5,425,367 A | 6/1995 | Shapiro et al. |
| 5,458,629 A | 10/1995 | Baudino et al. |
| 5,458,631 A | 10/1995 | Xavier |
| 5,464,446 A | 11/1995 | Dreessen et al. |
| 5,480,421 A | 1/1996 | Otten |
| 5,496,363 A | 3/1996 | Burgio et al. |
| 5,527,338 A | 6/1996 | Purdy |
| 5,531,778 A | 7/1996 | Maschino et al. |
| 5,562,722 A | 10/1996 | Racz et al. |
| 5,578,074 A | 11/1996 | Mirigian |
| 5,643,330 A | 7/1997 | Holsheimer |
| 5,669,882 A | 9/1997 | Pyles |
| 5,690,117 A | 11/1997 | Gilbert |
| 5,727,553 A | 3/1998 | Saad |
| 5,728,148 A | 3/1998 | Bostrom et al. |
| 5,730,628 A | 3/1998 | Hawkins |
| 5,755,750 A | 5/1998 | Petruska et al. |
| 5,759,471 A | 6/1998 | Malewicz |
| 5,760,341 A | 6/1998 | Laske et al. |
| 5,766,042 A | 6/1998 | Ries et al. |
| 5,769,877 A | 6/1998 | Barreras, Sr. |
| 5,843,146 A | 12/1998 | Cross, Jr. |
| 5,843,148 A | 12/1998 | Gijsbers |
| 5,846,226 A | 12/1998 | Urmey |
| 5,848,126 A | 12/1998 | Fujita et al. |
| 5,865,843 A | 2/1999 | Baudino |
| 5,871,487 A | 2/1999 | Warner et al. |
| 5,871,531 A | 2/1999 | Struble |
| 5,895,416 A | 4/1999 | Barreras |
| 5,902,236 A | 5/1999 | Iversen |
| 5,927,277 A | 7/1999 | Baudino et al. |
| 5,935,159 A | 8/1999 | Cross, Jr. et al. |
| 5,957,912 A | 9/1999 | Heitzmann |
| 5,957,965 A | 9/1999 | Moumane et al. |
| 5,957,968 A | 9/1999 | Belden et al. |
| 5,983,126 A | 11/1999 | Wittkampf |
| 6,042,432 A | 3/2000 | Hashizawa |
| 6,052,623 A | 4/2000 | Fenner et al. |
| 6,055,456 A | 4/2000 | Gerber |
| 6,066,165 A | 5/2000 | Racz |
| 6,078,839 A | 6/2000 | Carson |
| 6,104,960 A | 8/2000 | Duysens |
| 6,106,460 A | 8/2000 | Panescu et al. |
| 6,125,291 A | 9/2000 | Miesel et al. |
| 6,129,742 A | 10/2000 | Wu et al. |
| 6,134,459 A | 10/2000 | Roberts et al. |
| 6,134,477 A | 10/2000 | Knuteson |
| 6,144,866 A | 11/2000 | Miesel et al. |
| 6,154,678 A | 11/2000 | Lauro |
| 6,161,047 A | 12/2000 | King et al. |
| 6,163,727 A | 12/2000 | Errico |
| 6,175,769 B1 | 1/2001 | Errico et al. |
| 6,178,357 B1 | 1/2001 | Gliner et al. |
| 6,185,463 B1 | 2/2001 | Baudino |
| 6,192,278 B1 | 2/2001 | Werner et al. |
| 6,192,279 B1 | 2/2001 | Barreras, Sr. et al. |
| 6,198,952 B1 | 3/2001 | Miesel |
| 6,198,963 B1 | 3/2001 | Haim et al. |
| 6,205,356 B1 | 3/2001 | Holcomb |
| 6,205,359 B1 | 3/2001 | Boveja |
| 6,205,361 B1 | 3/2001 | Kuzma et al. |
| 6,210,417 B1 | 4/2001 | Baudino |
| 6,214,016 B1 | 4/2001 | Williams et al. |
| 6,216,045 B1 | 4/2001 | Black et al. |
| 6,248,112 B1 | 6/2001 | Gambale et al. |
| 6,249,965 B1 | 6/2001 | Bullara et al. |
| 6,251,115 B1 | 6/2001 | Williams et al. |
| 6,263,230 B1 | 7/2001 | Haynor et al. |
| 6,273,877 B1 | 8/2001 | West et al. |
| 6,292,702 B1 | 9/2001 | King et al. |
| 6,296,631 B2 | 10/2001 | Chow |
| 6,298,265 B1 | 10/2001 | Burgio |
| 6,300,359 B1 | 10/2001 | Flisak et al. |
| 6,304,785 B1 | 10/2001 | McCreery et al. |
| 6,308,103 B1 | 10/2001 | Gielen |
| 6,309,401 B1 | 10/2001 | Redko et al. |
| 6,319,241 B1 | 11/2001 | King et al. |
| 6,321,104 B1 | 11/2001 | Gielen et al. |
| 6,321,123 B1 | 11/2001 | Morris et al. |
| 6,364,899 B1 | 4/2002 | Dobak, III |
| 6,366,815 B1 | 4/2002 | Haugland et al. |
| 6,371,943 B1 | 4/2002 | Racz et al. |
| 6,374,140 B1 | 4/2002 | Rise |
| 6,393,323 B1 | 5/2002 | Sawan et al. |
| 6,393,327 B1 | 5/2002 | Scribner |
| 6,397,108 B1 | 5/2002 | Camps et al. |

(56) References Cited

U.S. PATENT DOCUMENTS

| | | |
|---|---|---|
| 6,415,187 B1 | 7/2002 | Kuzma et al. |
| 6,429,217 B1 | 8/2002 | Puskas |
| 6,438,418 B1 | 8/2002 | Swerdlow et al. |
| 6,442,435 B2 | 8/2002 | King et al. |
| 6,445,955 B1 | 9/2002 | Michelson et al. |
| 6,449,511 B1 | 9/2002 | Mintchev et al. |
| 6,451,030 B2 | 9/2002 | Li et al. |
| 6,456,874 B1 | 9/2002 | Hafer et al. |
| 6,463,328 B1 | 10/2002 | John |
| 6,464,682 B1 | 10/2002 | Snoke |
| 6,473,644 B1 | 10/2002 | Terry, Jr. et al. |
| 6,473,653 B1 | 10/2002 | Schallhorn et al. |
| 6,473,654 B1 | 10/2002 | Chinn |
| 6,474,341 B1 | 11/2002 | Hunter et al. |
| 6,477,427 B1 | 11/2002 | Stolz et al. |
| 6,480,820 B1 | 11/2002 | Clopton et al. |
| 6,482,049 B1 | 11/2002 | Swearingen |
| 6,484,059 B2 | 11/2002 | Gielen et al. |
| 6,493,590 B1 | 12/2002 | Wessman et al. |
| 6,493,592 B1 | 12/2002 | Leonard et al. |
| 6,512,949 B1 | 1/2003 | Combs et al. |
| 6,516,226 B1 | 2/2003 | Bishay et al. |
| 6,516,807 B1 | 2/2003 | Panescu et al. |
| 6,522,927 B1 | 2/2003 | Bishay et al. |
| 6,522,929 B2 | 2/2003 | Swing |
| 6,522,932 B1 | 2/2003 | Kuzma et al. |
| 6,529,774 B1 | 3/2003 | Greene |
| 6,540,568 B2 | 4/2003 | Miyazaki |
| 6,542,774 B2 | 4/2003 | Hill et al. |
| 6,542,780 B1 | 4/2003 | Leonard |
| 6,546,293 B2 | 4/2003 | Errico et al. |
| 6,549,797 B1 | 4/2003 | Leonard et al. |
| 6,549,810 B1 | 4/2003 | Leonard et al. |
| 6,549,812 B1 | 4/2003 | Smits |
| 6,553,264 B2 | 4/2003 | Redko et al. |
| 6,554,809 B2 | 4/2003 | Aves |
| 6,556,868 B2 | 4/2003 | Naritoku et al. |
| 6,556,869 B1 | 4/2003 | Leonard et al. |
| 6,556,873 B1 | 4/2003 | Smits |
| 6,560,491 B1 | 5/2003 | Leonard et al. |
| 6,587,719 B1 | 7/2003 | Barrett et al. |
| 6,587,733 B1 | 7/2003 | Cross, Jr. et al. |
| 6,600,956 B2 | 7/2003 | Maschino et al. |
| 6,605,094 B1 | 8/2003 | Mann et al. |
| 6,609,029 B1 | 8/2003 | Mann et al. |
| 6,622,038 B2 | 9/2003 | Barrett et al. |
| 6,622,051 B1 | 9/2003 | Bishay et al. |
| 6,704,605 B2 | 3/2004 | Soltis et al. |
| 6,714,822 B2 | 3/2004 | King et al. |
| 6,718,209 B2 | 4/2004 | Williamson et al. |
| 6,718,211 B2 | 4/2004 | Smits |
| 6,721,604 B1 | 4/2004 | Robinson et al. |
| 6,725,096 B2 | 4/2004 | Chinn et al. |
| 6,733,500 B2 | 5/2004 | Kelley et al. |
| 6,735,471 B2 | 5/2004 | Hill et al. |
| 6,741,892 B1 | 5/2004 | Meadows et al. |
| 6,741,893 B2 | 5/2004 | Smits |
| 6,745,079 B2 | 6/2004 | King |
| 6,754,539 B1 | 6/2004 | Erickson et al. |
| 6,758,854 B1 | 7/2004 | Butler et al. |
| 6,805,676 B2 | 10/2004 | Klint |
| 6,836,687 B2 | 12/2004 | Kelley et al. |
| 6,842,647 B1 | 1/2005 | Griffith et al. |
| 6,847,845 B2 | 1/2005 | Belden |
| 6,871,098 B2 | 3/2005 | Nuttin et al. |
| 6,875,571 B2 | 4/2005 | Crabtree et al. |
| 6,895,276 B2 | 5/2005 | Kast et al. |
| 6,895,283 B2 | 5/2005 | Erickson et al. |
| 6,901,289 B2 | 5/2005 | Dahl et al. |
| 6,902,547 B2 | 6/2005 | Aves et al. |
| 6,907,293 B2 | 6/2005 | Grill et al. |
| 6,907,295 B2 | 6/2005 | Gross et al. |
| 6,907,299 B2 | 6/2005 | Han |
| 6,909,918 B2 | 6/2005 | Stypulkowski |
| 6,929,656 B1 | 8/2005 | Lennox |
| 6,934,589 B2 | 8/2005 | Sundquist et al. |
| 6,944,501 B1 | 9/2005 | Pless |
| 6,961,621 B2 | 11/2005 | Krishnan et al. |
| 6,970,747 B2 | 11/2005 | Kokones et al. |
| 6,971,393 B1 | 12/2005 | Marno |
| 6,980,863 B2 | 12/2005 | van Venrooij et al. |
| 6,981,314 B2 | 1/2006 | Black et al. |
| 6,993,384 B2 | 1/2006 | Bradley et al. |
| 6,993,390 B2 | 1/2006 | Zappala |
| 6,999,819 B2 | 2/2006 | Swoyer et al. |
| 6,999,820 B2 | 2/2006 | Jordan |
| 7,010,856 B2 | 3/2006 | Suda et al. |
| 7,020,531 B1 | 3/2006 | Colliou et al. |
| 7,022,109 B1 | 4/2006 | Ditto |
| 7,047,078 B2 | 5/2006 | Boggs, II et al. |
| 7,047,082 B1 | 5/2006 | Schrom et al. |
| 7,047,084 B2 | 5/2006 | Erickson et al. |
| 7,051,419 B2 | 5/2006 | Schrom et al. |
| 7,069,078 B2 | 6/2006 | Houben |
| 7,069,083 B2 | 6/2006 | Finch et al. |
| 7,072,719 B2 | 7/2006 | Vinup et al. |
| 7,090,661 B2 | 8/2006 | Morris et al. |
| 7,107,097 B2 | 9/2006 | Stern et al. |
| 7,107,104 B2 | 9/2006 | Keravel et al. |
| 7,110,827 B2 | 9/2006 | Sage et al. |
| 7,127,298 B1 | 10/2006 | He et al. |
| 7,130,691 B2 | 10/2006 | Falci |
| 7,130,696 B2 | 10/2006 | Carter et al. |
| 7,133,722 B2 | 11/2006 | Hansen et al. |
| 7,136,695 B2 | 11/2006 | Pless et al. |
| 7,142,919 B2 | 11/2006 | Hine et al. |
| 7,145,229 B2 | 12/2006 | Maghribi et al. |
| 7,146,222 B2 | 12/2006 | Boling |
| 7,146,224 B2 | 12/2006 | King |
| 7,149,585 B2 | 12/2006 | Wessman et al. |
| 7,153,279 B2 | 12/2006 | Ayad |
| 7,153,307 B2 | 12/2006 | Scribner |
| 7,162,304 B1 | 1/2007 | Bradley |
| 7,164,944 B1 | 1/2007 | Kroll et al. |
| 7,164,951 B2 | 1/2007 | Ries et al. |
| 7,174,213 B2 | 2/2007 | Pless |
| 7,174,219 B2 | 2/2007 | Wahlstrand et al. |
| 7,181,288 B1 | 2/2007 | Rezai et al. |
| 7,182,726 B2 | 2/2007 | Williams et al. |
| 7,182,783 B2 | 2/2007 | Trieu |
| 7,184,838 B2 | 2/2007 | Cross, Jr. |
| 7,184,840 B2 | 2/2007 | Stolz et al. |
| 7,184,841 B1 | 2/2007 | Bodner et al. |
| 7,184,842 B2 | 2/2007 | Seifert et al. |
| 7,186,601 B2 | 3/2007 | Fukunaga et al. |
| 7,187,981 B2 | 3/2007 | Tanaka |
| 7,187,982 B2 | 3/2007 | Seifert et al. |
| 7,191,018 B2 | 3/2007 | Gielen et al. |
| 7,200,443 B2 | 4/2007 | Faul |
| 7,200,446 B2 | 4/2007 | Borkan |
| 7,206,642 B2 | 4/2007 | Pardo et al. |
| 7,209,787 B2 | 4/2007 | DiLorenzo |
| 7,211,103 B2 | 5/2007 | Greenberg et al. |
| 7,212,867 B2 | 5/2007 | Van Venrooij et al. |
| 7,225,016 B1 | 5/2007 | Koh |
| 7,236,834 B2 | 6/2007 | Christopherson et al. |
| 7,244,150 B1 | 7/2007 | Brase et al. |
| 7,270,650 B2 | 9/2007 | Morris et al. |
| 7,282,033 B2 | 10/2007 | Urmey |
| 7,299,095 B1 | 11/2007 | Barlow et al. |
| 7,340,306 B2 | 3/2008 | Barrett et al. |
| 7,363,076 B2 | 4/2008 | Yun et al. |
| 7,363,089 B2 | 4/2008 | Vinup et al. |
| 7,379,776 B1 | 5/2008 | Chitre et al. |
| 7,383,090 B2 | 6/2008 | O'Brien et al. |
| 7,386,341 B2 | 6/2008 | Hafer et al. |
| 7,386,350 B2 | 6/2008 | Vilims |
| 7,393,351 B2 | 7/2008 | Woloszko et al. |
| 7,421,297 B2 | 9/2008 | Giftakis et al. |
| 7,425,142 B1 | 9/2008 | Putz |
| 7,450,992 B1 | 11/2008 | Cameron |
| 7,455,666 B2 | 11/2008 | Purdy |
| 7,460,913 B2 | 12/2008 | Kuzma et al. |
| 7,463,917 B2 | 12/2008 | Martinez |

(56) References Cited

U.S. PATENT DOCUMENTS

| | | |
|---|---|---|
| 7,486,991 B2 | 2/2009 | Libbus et al. |
| 7,493,159 B2 | 2/2009 | Hrdlicka et al. |
| 7,496,404 B2 | 2/2009 | Meadows et al. |
| 7,499,755 B2 | 3/2009 | Cross, Jr. |
| 7,500,985 B2 | 3/2009 | Saadat |
| 7,502,652 B2 | 3/2009 | Gaunt et al. |
| 7,546,164 B2 | 6/2009 | King |
| 7,580,753 B2 | 8/2009 | Kim et al. |
| 7,584,004 B2 | 9/2009 | Caparso et al. |
| 7,590,454 B2 | 9/2009 | Garabedian et al. |
| 7,604,644 B2 | 10/2009 | Schulte et al. |
| 7,613,516 B2 | 11/2009 | Cohen et al. |
| 7,613,524 B2 | 11/2009 | Jordan |
| 7,616,988 B2 | 11/2009 | Stahmann et al. |
| 7,617,003 B2 | 11/2009 | Caparso et al. |
| 7,617,006 B2 | 11/2009 | Metzler et al. |
| 7,623,919 B2 | 11/2009 | Goetz et al. |
| 7,627,380 B2 | 12/2009 | Podhajsky et al. |
| 7,640,064 B2 | 12/2009 | Swoyer |
| 7,672,734 B2 | 3/2010 | Anderson et al. |
| 7,684,873 B2 | 3/2010 | Gerber |
| 7,689,284 B2 | 3/2010 | Imran et al. |
| 7,702,379 B2 | 4/2010 | Avinash et al. |
| 7,769,441 B2 | 8/2010 | Foreman et al. |
| 7,769,442 B2 | 8/2010 | Shafer |
| 7,769,472 B2 | 8/2010 | Gerber |
| 7,781,806 B2 | 8/2010 | VanBuskirk et al. |
| 7,797,057 B2 | 9/2010 | Harris |
| 7,805,188 B2 | 9/2010 | Brushey |
| 7,810,233 B2 | 10/2010 | Krulevitch et al. |
| 7,810,996 B1 | 10/2010 | Giphart et al. |
| 7,829,694 B2 | 11/2010 | Kaemmerer |
| 7,831,307 B1 | 11/2010 | Moffitt |
| 7,844,343 B2 | 11/2010 | Wahlstrand et al. |
| 7,853,321 B2 | 12/2010 | Jaax et al. |
| 7,853,330 B2 | 12/2010 | Bradley et al. |
| 7,860,568 B2 | 12/2010 | Deininger et al. |
| 7,881,806 B2 | 2/2011 | Horrigan et al. |
| 7,904,149 B2 | 3/2011 | Gerber |
| 7,922,738 B2 | 4/2011 | Eichmann et al. |
| 7,996,055 B2 | 8/2011 | Hauck et al. |
| 8,000,805 B2 | 8/2011 | Swoyer et al. |
| 8,010,207 B2 | 8/2011 | Smits et al. |
| 8,014,873 B2 | 9/2011 | Jones et al. |
| 8,019,439 B2 | 9/2011 | Kuzma et al. |
| 8,019,443 B2 | 9/2011 | Schleicher et al. |
| 8,024,035 B2 | 9/2011 | Dobak, III |
| 8,036,756 B2 | 10/2011 | Swoyer et al. |
| 8,060,207 B2 | 11/2011 | Wallace et al. |
| 8,078,280 B2 | 12/2011 | Sage |
| 8,123,807 B2 | 2/2012 | Kim |
| 8,131,357 B2 | 3/2012 | Bradley |
| 8,140,172 B1 | 3/2012 | Jones et al. |
| 8,197,494 B2 | 6/2012 | Jaggi et al. |
| 8,200,343 B2 | 6/2012 | Gerber et al. |
| 8,204,569 B2 | 6/2012 | Gerber et al. |
| 8,224,459 B1 | 7/2012 | Pianca et al. |
| 8,229,573 B2 | 7/2012 | Chen et al. |
| 8,249,720 B2 | 8/2012 | Verzal et al. |
| 8,255,057 B2 | 8/2012 | Fang et al. |
| 8,301,268 B1 | 10/2012 | Jones et al. |
| 8,303,502 B2 | 11/2012 | Washburn et al. |
| 8,355,791 B2 | 1/2013 | Moffitt |
| 8,355,797 B2 | 1/2013 | Caparso et al. |
| 8,412,349 B2 | 4/2013 | Barker |
| 8,467,883 B2 | 6/2013 | Chen |
| 8,483,845 B2 | 7/2013 | Sage |
| 8,494,652 B2 | 7/2013 | Cantlon et al. |
| 8,548,601 B2 | 10/2013 | Chinn et al. |
| 8,634,934 B2 | 1/2014 | Kokones |
| 8,644,954 B2 | 2/2014 | Jaax et al. |
| 8,676,331 B2 | 3/2014 | Parker |
| 8,731,671 B2 | 5/2014 | Rodby et al. |
| 8,761,902 B2 | 7/2014 | Kulle |
| 8,805,519 B2 | 8/2014 | Parker et al. |
| 9,026,226 B2 | 5/2015 | Gerber et al. |
| 9,089,672 B2 | 7/2015 | Hendriksen et al. |
| 9,138,574 B2 | 9/2015 | Kern et al. |
| 9,265,935 B2 | 2/2016 | Thacker |
| 9,358,388 B2 | 6/2016 | Parker et al. |
| 9,409,010 B2 | 8/2016 | Farhat et al. |
| 9,504,839 B2 | 11/2016 | Leven |
| 9,510,818 B2 | 12/2016 | Lee |
| 9,517,332 B2 | 12/2016 | Olson et al. |
| 9,517,334 B2 | 12/2016 | Barner et al. |
| 9,687,649 B2 | 1/2017 | Thacker et al. |
| 9,889,293 B2 | 2/2018 | Siegel et al. |
| 9,987,482 B2 | 6/2018 | Nageri et al. |
| 10,016,604 B2 | 7/2018 | Biele et al. |
| 10,092,744 B2 | 10/2018 | Sommer et al. |
| 10,105,536 B2 | 10/2018 | Orts et al. |
| 2001/0000800 A1 | 5/2001 | Partridge et al. |
| 2001/0014820 A1 | 8/2001 | Gielen et al. |
| 2001/0016765 A1 | 8/2001 | Gielen et al. |
| 2001/0023368 A1 | 9/2001 | Black et al. |
| 2001/0025192 A1 | 9/2001 | Gerber et al. |
| 2001/0027336 A1 | 10/2001 | Gielen et al. |
| 2001/0031989 A1 | 10/2001 | Swing |
| 2001/0053885 A1 | 12/2001 | Gielen et al. |
| 2002/0022872 A1 | 2/2002 | Gielen et al. |
| 2002/0022873 A1 | 2/2002 | Erickson et al. |
| 2002/0052640 A1 | 5/2002 | Bigus et al. |
| 2002/0072787 A1 | 6/2002 | Partridge et al. |
| 2002/0107553 A1 | 8/2002 | Hill et al. |
| 2002/0111661 A1 | 8/2002 | Cross et al. |
| 2002/0128700 A1 | 9/2002 | Cross |
| 2002/0156513 A1 | 10/2002 | Borkan |
| 2002/0161417 A1 | 10/2002 | Scribner |
| 2002/0173718 A1 | 11/2002 | Frisch et al. |
| 2002/0177887 A1 | 11/2002 | Krebs |
| 2002/0198568 A1 | 12/2002 | Hafer et al. |
| 2003/0018365 A1 | 1/2003 | Loeb |
| 2003/0018367 A1 | 1/2003 | DiLorenzo |
| 2003/0032997 A1 | 2/2003 | Pianca et al. |
| 2003/0055476 A1 | 3/2003 | Vinup et al. |
| 2003/0062048 A1 | 4/2003 | Gradon et al. |
| 2003/0083697 A1 | 5/2003 | Baudino et al. |
| 2003/0083724 A1 | 5/2003 | Jog et al. |
| 2003/0088245 A1 | 5/2003 | Woloszko et al. |
| 2003/0097165 A1 | 5/2003 | Krulevitch et al. |
| 2003/0097166 A1 | 5/2003 | Krulevitch et al. |
| 2003/0114752 A1 | 6/2003 | Henderson et al. |
| 2003/0114895 A1 | 6/2003 | Gordon et al. |
| 2003/0120150 A1 | 6/2003 | Govari |
| 2003/0136418 A1 | 7/2003 | Behm |
| 2003/0187483 A1 | 10/2003 | Grey et al. |
| 2003/0199948 A1 | 10/2003 | Kokones et al. |
| 2003/0199949 A1 | 10/2003 | Pardo |
| 2003/0199951 A1 | 10/2003 | Pardo et al. |
| 2003/0199952 A1 | 10/2003 | Stolz et al. |
| 2003/0199953 A1 | 10/2003 | Stolz et al. |
| 2003/0199962 A1 | 10/2003 | Struble et al. |
| 2003/0204206 A1 | 10/2003 | Padua et al. |
| 2003/0208247 A1 | 11/2003 | Spinelli et al. |
| 2003/0216792 A1 | 11/2003 | Levin et al. |
| 2003/0220677 A1 | 11/2003 | Doan et al. |
| 2003/0229387 A1 | 12/2003 | Cross et al. |
| 2003/0233134 A1 | 12/2003 | Greenberg et al. |
| 2004/0015133 A1 | 1/2004 | Karim |
| 2004/0015188 A1 | 1/2004 | Coulter |
| 2004/0015205 A1 | 1/2004 | Whitehurst et al. |
| 2004/0015206 A1 | 1/2004 | Bishay et al. |
| 2004/0024428 A1 | 2/2004 | Barrett et al. |
| 2004/0024439 A1 | 2/2004 | Riso |
| 2004/0024440 A1 | 2/2004 | Cole |
| 2004/0087877 A1 | 5/2004 | Besz et al. |
| 2004/0088009 A1 | 5/2004 | Degroot |
| 2004/0088021 A1 | 5/2004 | Cameron et al. |
| 2004/0088033 A1 | 5/2004 | Smits et al. |
| 2004/0088034 A1 | 5/2004 | Smits et al. |
| 2004/0093053 A1 | 5/2004 | Gerber et al. |
| 2004/0097803 A1 | 5/2004 | Panescu |
| 2004/0111139 A1 | 6/2004 | McCreery |
| 2004/0122475 A1 | 6/2004 | Myrick et al. |

(56) References Cited

U.S. PATENT DOCUMENTS

| | | |
|---|---|---|
| 2004/0127942 A1 | 7/2004 | Yomtov et al. |
| 2004/0138536 A1 | 7/2004 | Frei et al. |
| 2004/0152958 A1 | 8/2004 | Frei et al. |
| 2004/0162601 A1 | 8/2004 | Smits |
| 2004/0172085 A1 | 9/2004 | Knudson et al. |
| 2004/0172100 A1 | 9/2004 | Humayun et al. |
| 2004/0176683 A1 | 9/2004 | Whitin et al. |
| 2004/0186528 A1 | 9/2004 | Ries et al. |
| 2004/0186543 A1 | 9/2004 | King et al. |
| 2004/0186544 A1 | 9/2004 | King |
| 2004/0210290 A1 | 10/2004 | Omar-Pasha |
| 2004/0210291 A1 | 10/2004 | Erickson et al. |
| 2004/0215301 A1 | 10/2004 | Lokhoff et al. |
| 2004/0215305 A1 | 10/2004 | Sage |
| 2004/0215307 A1 | 10/2004 | Michels et al. |
| 2004/0236387 A1 | 11/2004 | Fang et al. |
| 2004/0243206 A1 | 12/2004 | Tadlock |
| 2004/0260356 A1 | 12/2004 | Kara et al. |
| 2005/0004417 A1 | 1/2005 | Nelson et al. |
| 2005/0004638 A1 | 1/2005 | Cross |
| 2005/0004639 A1 | 1/2005 | Erickson |
| 2005/0010260 A1 | 1/2005 | Gerber |
| 2005/0015128 A1 | 1/2005 | Rezai et al. |
| 2005/0020970 A1 | 1/2005 | Gerber |
| 2005/0021069 A1 | 1/2005 | Feuer et al. |
| 2005/0021119 A1 | 1/2005 | Sage |
| 2005/0027325 A1 | 2/2005 | Lahti et al. |
| 2005/0027338 A1 | 2/2005 | Hill |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0033371 A1 | 2/2005 | Sommer et al. |
| 2005/0049486 A1 | 3/2005 | Urquhart et al. |
| 2005/0049648 A1 | 3/2005 | Cohen et al. |
| 2005/0049650 A1 | 3/2005 | Nuttin et al. |
| 2005/0049663 A1 | 3/2005 | Harris et al. |
| 2005/0049664 A1 | 3/2005 | Harris et al. |
| 2005/0065588 A1 | 3/2005 | Zhao et al. |
| 2005/0070969 A1 | 3/2005 | Gerber |
| 2005/0070974 A1 | 3/2005 | Knudson et al. |
| 2005/0070982 A1 | 3/2005 | Heruth et al. |
| 2005/0070987 A1 | 3/2005 | Erickson |
| 2005/0075684 A1 | 4/2005 | Phillips et al. |
| 2005/0075702 A1 | 4/2005 | Shafer |
| 2005/0075707 A1 | 4/2005 | Meadows et al. |
| 2005/0085870 A1 | 4/2005 | Goroszeniuk |
| 2005/0090885 A1 | 4/2005 | Harris et al. |
| 2005/0096718 A1 | 5/2005 | Gerber et al. |
| 2005/0107753 A1 | 5/2005 | Rezai et al. |
| 2005/0107859 A1 | 5/2005 | Daglow et al. |
| 2005/0107861 A1 | 5/2005 | Harris et al. |
| 2005/0113878 A1 | 5/2005 | Gerber |
| 2005/0119713 A1 | 6/2005 | Whitehurst et al. |
| 2005/0131486 A1 | 6/2005 | Boveja et al. |
| 2005/0131506 A1 | 6/2005 | Rezai et al. |
| 2005/0137648 A1 | 6/2005 | Cosendai et al. |
| 2005/0137667 A1 | 6/2005 | Omar-Pasha et al. |
| 2005/0137668 A1 | 6/2005 | Khan |
| 2005/0138791 A1 | 6/2005 | Black et al. |
| 2005/0138792 A1 | 6/2005 | Black et al. |
| 2005/0165458 A1 | 7/2005 | Boveja et al. |
| 2005/0165465 A1 | 7/2005 | Pianca et al. |
| 2005/0171587 A1 | 8/2005 | Daglow et al. |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182424 A1 | 8/2005 | Schulte et al. |
| 2005/0182425 A1 | 8/2005 | Schulte et al. |
| 2005/0187600 A1 | 8/2005 | Hunter et al. |
| 2005/0203599 A1 | 9/2005 | Garabedian et al. |
| 2005/0209665 A1 | 9/2005 | Hunter et al. |
| 2005/0209667 A1 | 9/2005 | Erickson et al. |
| 2005/0216070 A1 | 9/2005 | Boveja et al. |
| 2005/0222635 A1 | 10/2005 | Krakovsky |
| 2005/0222642 A1 | 10/2005 | Przybyszewski et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0228221 A1 | 10/2005 | Hirakawa |
| 2005/0240229 A1 | 10/2005 | Whitehurst et al. |
| 2005/0246003 A1 | 11/2005 | Black et al. |
| 2005/0246004 A1 | 11/2005 | Cameron et al. |
| 2005/0283216 A1 | 12/2005 | Pyles |
| 2005/0288566 A1 | 12/2005 | Levendusky et al. |
| 2006/0004429 A1 | 1/2006 | Mrva et al. |
| 2006/0025832 A1 | 2/2006 | O'Keeffe et al. |
| 2006/0041277 A1 | 2/2006 | Deem et al. |
| 2006/0052765 A1 | 3/2006 | Pyles et al. |
| 2006/0085070 A1 | 4/2006 | Kim |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0106440 A1 | 5/2006 | Chandran et al. |
| 2006/0111768 A1 | 5/2006 | Wessman et al. |
| 2006/0122654 A1 | 6/2006 | Bradley et al. |
| 2006/0127158 A1 | 6/2006 | Olson et al. |
| 2006/0161236 A1 | 7/2006 | King |
| 2006/0167525 A1 | 7/2006 | King |
| 2006/0168805 A1 | 8/2006 | Hegland et al. |
| 2006/0173262 A1 | 8/2006 | Hegland et al. |
| 2006/0200218 A1 | 9/2006 | Wahlstrand |
| 2006/0241725 A1 | 10/2006 | Libbus et al. |
| 2006/0247569 A1 | 11/2006 | Bertrand et al. |
| 2006/0247747 A1 | 11/2006 | Olsen et al. |
| 2006/0247748 A1 | 11/2006 | Wahlstrand et al. |
| 2006/0247749 A1 | 11/2006 | Colvin |
| 2006/0253182 A1 | 11/2006 | King |
| 2006/0259095 A1 | 11/2006 | Wyler et al. |
| 2006/0259110 A1 | 11/2006 | Wallace et al. |
| 2006/0264122 A1 | 11/2006 | Aman et al. |
| 2006/0265024 A1 | 11/2006 | Goetz et al. |
| 2006/0265037 A1 | 11/2006 | Kuzma |
| 2006/0271137 A1 | 11/2006 | Stanton-Hicks |
| 2007/0032836 A1 | 2/2007 | Thrope et al. |
| 2007/0038052 A1 | 2/2007 | Swoyer et al. |
| 2007/0043403 A1 | 2/2007 | Blamey et al. |
| 2007/0048289 A1 | 3/2007 | Grandjean |
| 2007/0050004 A1 | 3/2007 | Swoyer et al. |
| 2007/0050005 A1 | 3/2007 | Lauro |
| 2007/0055332 A1 | 3/2007 | Swoyer |
| 2007/0088414 A1 | 4/2007 | Campbell et al. |
| 2007/0100386 A1 | 5/2007 | Tronnes et al. |
| 2007/0100391 A1 | 5/2007 | Armstrong |
| 2007/0100408 A1 | 5/2007 | Gerber |
| 2007/0106144 A1 | 5/2007 | Squeri |
| 2007/0106289 A1 | 5/2007 | O'Sullivan |
| 2007/0112404 A1 | 5/2007 | Mann et al. |
| 2007/0118198 A1 | 5/2007 | Prager |
| 2007/0135881 A1 | 6/2007 | Vilims |
| 2007/0149048 A1 | 6/2007 | O'Brien et al. |
| 2007/0150026 A1 | 6/2007 | Bourget et al. |
| 2007/0150036 A1 | 6/2007 | Anderson |
| 2007/0191709 A1 | 8/2007 | Swanson |
| 2007/0191903 A1 | 8/2007 | Bruinstroop |
| 2007/0191904 A1 | 8/2007 | Libbus et al. |
| 2007/0191909 A1 | 8/2007 | Ameri et al. |
| 2007/0203540 A1 | 8/2007 | Goetz et al. |
| 2007/0208394 A1 | 9/2007 | King et al. |
| 2007/0213795 A1 | 9/2007 | Bradley et al. |
| 2007/0249901 A1 | 10/2007 | Ohline et al. |
| 2007/0255295 A1 | 11/2007 | Starkbaum et al. |
| 2007/0255364 A1 | 11/2007 | Gerber et al. |
| 2007/0255365 A1 | 11/2007 | Gerber et al. |
| 2007/0255366 A1 | 11/2007 | Gerber et al. |
| 2007/0255367 A1 | 11/2007 | Gerber et al. |
| 2007/0255370 A1 | 11/2007 | Bonde et al. |
| 2007/0255371 A1 | 11/2007 | Bonde et al. |
| 2007/0260290 A1 | 11/2007 | Hara et al. |
| 2007/0261115 A1 | 11/2007 | Gerber et al. |
| 2008/0039738 A1 | 2/2008 | Dinsmoor et al. |
| 2008/0058875 A1 | 3/2008 | Greenberg et al. |
| 2008/0097475 A1 | 4/2008 | Jaggi et al. |

(56) References Cited

U.S. PATENT DOCUMENTS

| | | |
|---|---|---|
| 2008/0103569 A1 | 5/2008 | Gerber |
| 2008/0103572 A1 | 5/2008 | Gerber |
| 2008/0103573 A1 | 5/2008 | Gerber |
| 2008/0103576 A1 | 5/2008 | Gerber |
| 2008/0103578 A1 | 5/2008 | Gerber |
| 2008/0103579 A1 | 5/2008 | Gerber |
| 2008/0114433 A1 | 5/2008 | Sage |
| 2008/0125833 A1 | 5/2008 | Bradley et al. |
| 2008/0132926 A1 | 6/2008 | Eichmann et al. |
| 2008/0140087 A1 | 6/2008 | Barbagli |
| 2008/0140152 A1 | 6/2008 | Imran et al. |
| 2008/0177339 A1 | 7/2008 | Bolea et al. |
| 2008/0183221 A1 | 7/2008 | Burdulis |
| 2008/0234791 A1 | 9/2008 | Arle et al. |
| 2008/0262430 A1 | 10/2008 | Anderson et al. |
| 2008/0275467 A1 | 11/2008 | Liao et al. |
| 2008/0300651 A1 | 12/2008 | Gerber et al. |
| 2008/0319311 A1 | 12/2008 | Hamadeh |
| 2009/0048638 A1 | 2/2009 | Rey et al. |
| 2009/0069803 A1 | 3/2009 | Starkebaum |
| 2009/0125060 A1 | 5/2009 | Rivard et al. |
| 2009/0132017 A1 | 5/2009 | Erickson et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0210029 A1 | 8/2009 | Tsui |
| 2009/0216306 A1 | 8/2009 | Barker |
| 2009/0248118 A1 | 10/2009 | Bradley |
| 2009/0259280 A1 | 10/2009 | Wilkin et al. |
| 2009/0270940 A1 | 10/2009 | Deininger et al. |
| 2009/0299444 A1* | 12/2009 | Boling ............ A61N 1/0558 607/118 |
| 2009/0319013 A1 | 12/2009 | Boling et al. |
| 2010/0069736 A1 | 3/2010 | Finneran et al. |
| 2010/0094115 A1 | 4/2010 | Pond, Jr. et al. |
| 2010/0094116 A1 | 4/2010 | Silverstein |
| 2010/0114283 A1 | 5/2010 | King |
| 2010/0137938 A1 | 6/2010 | Kishawi |
| 2010/0137944 A1 | 6/2010 | Zhu |
| 2010/0137955 A1 | 6/2010 | Milijasevic et al. |
| 2010/0152538 A1 | 6/2010 | Gleason et al. |
| 2010/0204569 A1 | 8/2010 | Burnside et al. |
| 2010/0211135 A1 | 8/2010 | Caparso et al. |
| 2010/0256696 A1 | 10/2010 | Schleicher et al. |
| 2010/0267265 A1 | 10/2010 | Dilmaghanian |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274336 A1 | 10/2010 | Nguyen-Stella et al. |
| 2010/0280570 A1 | 11/2010 | Sturm et al. |
| 2010/0286551 A1 | 11/2010 | Harlev et al. |
| 2010/0292769 A1 | 11/2010 | Brounstein et al. |
| 2010/0298905 A1 | 11/2010 | Simon |
| 2010/0305631 A1 | 12/2010 | Bradley et al. |
| 2010/0318165 A1 | 12/2010 | Harris |
| 2010/0324414 A1 | 12/2010 | Harlev et al. |
| 2010/0324570 A1 | 12/2010 | Rooney et al. |
| 2011/0004281 A1 | 1/2011 | Jones |
| 2011/0009927 A1 | 1/2011 | Parker et al. |
| 2011/0031961 A1 | 2/2011 | Durand et al. |
| 2011/0046617 A1 | 2/2011 | Thompson et al. |
| 2011/0071593 A1 | 3/2011 | Parker |
| 2011/0106052 A1 | 5/2011 | Chiang et al. |
| 2011/0106100 A1 | 5/2011 | Bischoff |
| 2011/0160568 A1 | 6/2011 | Seeley et al. |
| 2011/0166582 A1 | 7/2011 | Syed et al. |
| 2011/0178573 A1 | 7/2011 | Nguyen-Stella et al. |
| 2011/0202097 A1 | 8/2011 | Bonde et al. |
| 2011/0224682 A1 | 9/2011 | Westlund et al. |
| 2011/0230943 A1 | 9/2011 | Johnson et al. |
| 2011/0245903 A1 | 10/2011 | Schulte et al. |
| 2012/0083709 A1 | 4/2012 | Parker et al. |
| 2012/0083856 A1 | 4/2012 | Thacker |
| 2012/0173946 A1 | 7/2012 | Terry et al. |
| 2012/0209285 A1 | 8/2012 | Barker et al. |
| 2012/0232626 A1 | 9/2012 | Daglow |
| 2013/0041445 A1 | 2/2013 | Erickson et al. |
| 2013/0066331 A1 | 3/2013 | Chitre et al. |
| 2013/0066411 A1 | 3/2013 | Thacker et al. |
| 2013/0096642 A1 | 4/2013 | Wingeier |
| 2013/0116754 A1 | 5/2013 | Sharma et al. |
| 2013/0138191 A1 | 5/2013 | Jones |
| 2013/0245739 A1 | 9/2013 | Arber |
| 2013/0261697 A1 | 10/2013 | Parker |
| 2013/0268037 A1 | 10/2013 | Schulte et al. |
| 2013/0296957 A1 | 11/2013 | Tronnes |
| 2014/0031837 A1 | 1/2014 | Perryman et al. |
| 2014/0081362 A1 | 3/2014 | Wicklund |
| 2014/0155973 A1 | 6/2014 | Grigsby et al. |
| 2014/0180305 A1 | 6/2014 | Pianca |
| 2014/0200627 A1 | 7/2014 | Parker et al. |
| 2014/0303685 A1 | 10/2014 | Rosenberg et al. |
| 2014/0343564 A1 | 11/2014 | Feler et al. |
| 2014/0343656 A1 | 11/2014 | Wechter |
| 2015/0005859 A1 | 1/2015 | Thacker et al. |
| 2015/0012077 A1 | 1/2015 | Parker et al. |
| 2015/0141787 A1 | 5/2015 | Bonde |
| 2015/0151114 A1 | 6/2015 | Black et al. |
| 2015/0290461 A1 | 10/2015 | Mln |
| 2016/0059006 A1 | 3/2016 | Doan et al. |
| 2016/0302827 A1 | 10/2016 | Chitre et al. |
| 2016/0346553 A1 | 12/2016 | Black |
| 2016/0354609 A1 | 12/2016 | Parker et al. |
| 2016/0360993 A1 | 12/2016 | Thacker et al. |
| 2017/0151428 A1 | 6/2017 | Schleicher et al. |
| 2017/0151432 A1 | 6/2017 | Christopherson et al. |
| 2017/0189676 A1 | 7/2017 | Bentley et al. |
| 2017/0252032 A1 | 9/2017 | Hiorth et al. |
| 2017/0281949 A1 | 10/2017 | Thacker |
| 2018/0099147 A1 | 4/2018 | Kane et al. |
| 2018/0296827 A1 | 10/2018 | Pianca et al. |
| 2018/0311494 A1 | 11/2018 | Wang et al. |
| 2019/0001122 A1 | 1/2019 | Ganty et al. |
| 2019/0105503 A1 | 4/2019 | Leven |
| 2019/0308010 A1 | 10/2019 | Sunkeri et al. |

FOREIGN PATENT DOCUMENTS

| | | |
|---|---|---|
| EP | 2086630 | 11/2010 |
| EP | 1477203 | 9/2015 |
| EP | 1334745 | 5/2017 |
| EP | 2539016 | 11/2017 |
| EP | 2731671 | 4/2019 |
| WO | WO-9003824 A1 | 4/1990 |
| WO | WO-2006045091 A2 | 4/2006 |
| WO | WO-2006055388 A2 | 5/2006 |
| WO | WO-2008094952 | 8/2008 |
| WO | WO-2009097224 A1 | 8/2009 |
| WO | WO-2009129329 A1 | 10/2009 |
| WO | WO-2011014570 A1 | 2/2011 |
| WO | WO-2014209814 | 12/2014 |

OTHER PUBLICATIONS

Intrel® Model 7490 / 7491 Extensions for Spinal Cord Stimulation (SCS), Medtronic Neuro, Minneapolis, MN 1984, 9 pages.

Kulkarni et al., "A two-layered forward model of tissue for electrical; impedance tomography," Physiol Meas., 30(6); pp. 1-24, Jun. 2009.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Medtronic, "Physician and Hospital Staff Manual," InterStrim System, Neurological Division. 93 pages, undated.

International Search Report and Written Opinion for International Patent Application No. PCT/US2019/024573, Applicant: Nevro Corp., dated Aug. 8, 2019, 10 pages.

(56) References Cited

OTHER PUBLICATIONS

Extended European Search Report and Written Opinion for European Patent Application No. 19778392.1, Applicant: Nevro Corp., dated Nov. 5, 2021, 6 pages.

* cited by examiner

LEADS HAVING SIDEWALL OPENINGS, AND ASSOCIATED SYSTEMS AND METHODS

CROSS-REFERENCE TO RELATED APPLICATION

The present application claims priority to U.S. Provisional Application No. 62/650,111, filed on Mar. 29, 2018, and incorporated herein by reference.

TECHNICAL FIELD

The present technology is directed generally to leads having sidewall openings for receiving stylets, e.g., to steer and position the leads within a patient and/or with respect to a pulse generator, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes or contacts and the SCS leads are typically implanted either surgically or externally through a needle inserted into the epidural space, often with the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. The electrical pulses can generate sensations that mask or otherwise alter the patient's sensation of pain. For example, in many cases, patients report a tingling or paresthesia that is perceived as more pleasant and/or less uncomfortable than the underlying pain sensation. In other cases, the patients can receive pain relief without paresthesia or other sensations.

DETAILED DESCRIPTION

Figure 1A:
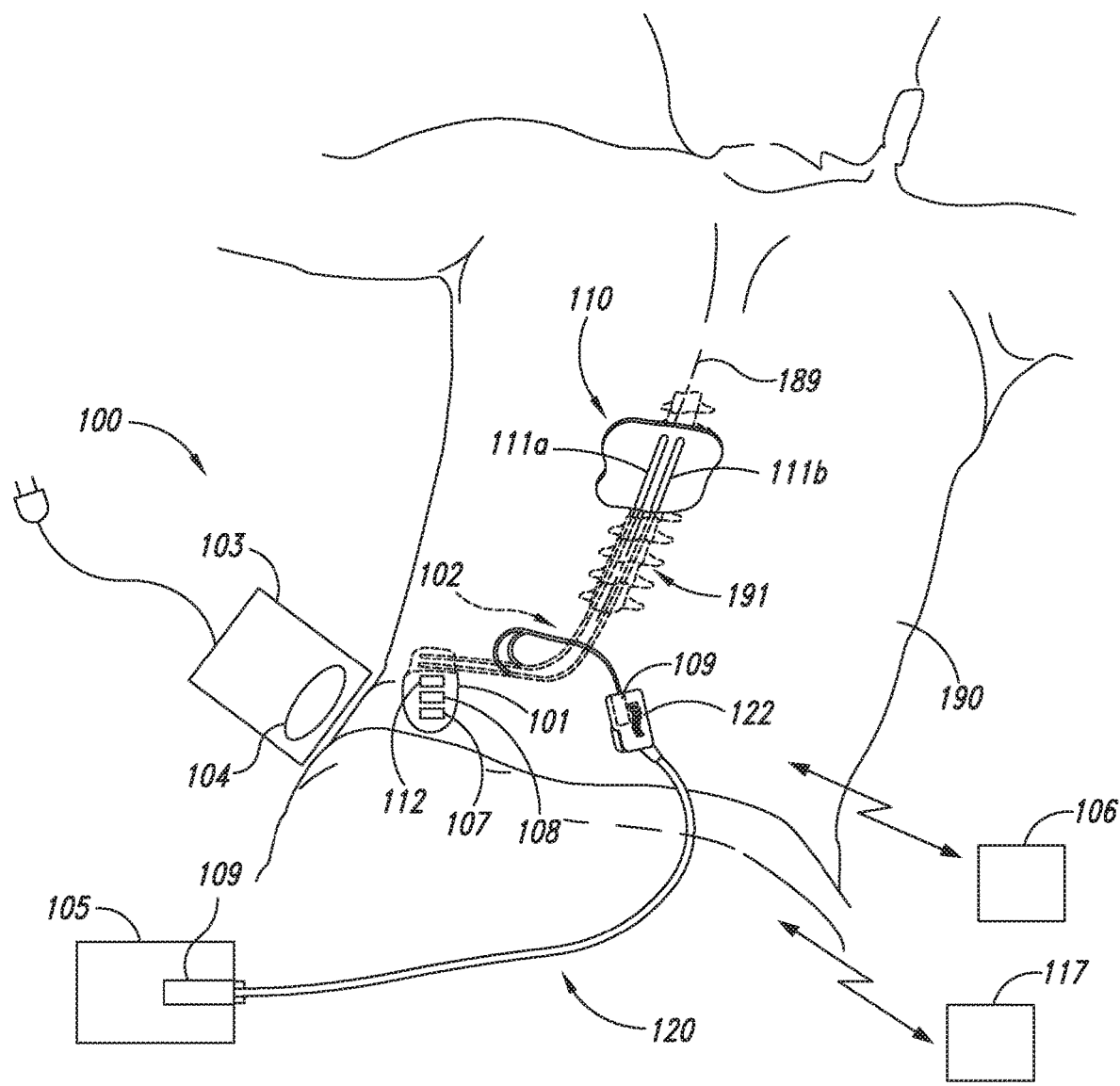
FIG. 1A is a partially schematic illustration of an implantable spinal cord modulation system positioned at the spine to deliver therapeutic signals in accordance with some embodiments of the present technology.

The present technology is directed generally to leads having a sidewall with one or more openings (e.g., sidewall openings) and associated systems and methods. In some embodiments, the leads are implantable leads. In some embodiments, the implantable leads are modulation leads. For example, the modulation leads can be spinal cord stimulation (SCS) leads, deep brain stimulation (DBS) leads, peripheral nerve stimulation (PNS) leads, and/or sacral (e.g., non-spinal cord region, such as horsetail region) stimulation leads. In some embodiments, the leads are percutaneous leads. In at least some contexts, the leads include a lumen extending from the sidewall opening to a distal portion of the lead. The lumen can be configured to receive a stylet shaped and sized to be removably inserted into the lumen through the opening. The lead can further include a proximal portion, and an intermediate portion disposed between the distal portion and the proximal portion. Together, the intermediate portion and the distal portion comprise a steerable portion of the lead. Leads configured in accordance with the present technology can have improved steering by virtue of one or more openings disposed in the intermediate portion of the lead. As a result, longer leads can be steered similarly to shorter leads. Furthermore, leads configured in accordance with the present technology can reduce the duration of a procedure associated with inserting and/or positioning a lead, and/or can increase the accuracy and/or the efficiency of these procedures.

In other embodiments, the lumen can extend from the sidewall opening (located at the intermediate portion of a lead) to a proximal end of the lead. Accordingly, the stylet can provide support to the proximal portion of the lead. The practitioner can use this arrangement to improve the ease and accuracy with which the proximal portion of the lead is inserted into a pulse generator or other device that provides electrical or other communication with the distal end of the lead. As will be described in further detail below, whether the sidewall opening or openings facilitate support of the distal end of the lead and/or the proximal end of the lead, the opening(s) can improve the efficiency, accuracy, and/or repeatability of insertion processes performed with the lead.

Specific details of some embodiments of the present technology are described below with reference to representative spinal cord modulation leads to provide a thorough understanding of these embodiments, but some embodiments can have other arrangements. Several details describing structures or processes that are well-known and often associated with leads and associated devices but that may unnecessarily obscure some significant aspects of the disclosure are not set forth in the following description for purposes of clarity. Moreover, although the following disclosure sets forth some embodiments of different aspects of the technology, some embodiments of the technology can have different configurations, different components, and/or different procedures than those described below. Some embodiments may eliminate particular components and/or procedures. A person of ordinary skill in the relevant art, therefore, will understand that the present technology which includes associated devices, systems, and procedures, may include some embodiments with additional elements or steps, and/or may include some embodiments without several of the features or steps shown and described below with reference to FIGS. 1A-6D. Several aspects of overall systems in accordance with the disclosed technology are described with reference to FIGS. 1A and 1B, and features specific to leads having sidewall openings are then discussed with reference to FIGS. 2A-6D.

1.0 Overview

FIG. 1A schematically illustrates a representative patient therapy system 100 for providing relief from chronic pain and/or other conditions, arranged relative to the general anatomy of a patient's spinal column 191. While system 100 is illustrated as an SCS system, the system 100 can also be configured for DBS, PNS, sacral stimulation, and/or other types of stimulation involving leads, such as implantable leads or percutaneous leads. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms "signal delivery device," "lead," and/or "lead body" include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, which is incorporated herein by reference in its entirety.

In some embodiments, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In some embodiments, the leads 111 may be implanted at a vertebral level ranging from, for example, about T8 to about T12. In some embodiments, one or more signal delivery devices can be implanted at other vertebral levels, e.g., as disclosed in U.S. Patent Application Publication No. 2013/0066411, which is incorporated herein by reference in its entirety. For example, the one or more signal delivery devices can be implanted using methods and at locations suitable for DBS, PNS, sacral stimulation, and/or other types of stimulation involving implantable leads.

The signal generator 101 can transmit signals (e.g., electrical signals) to the signal delivery elements 110 that up-regulate (e.g., excite) and/or down-regulate (e.g., suppress) target nerves. As used herein, and unless otherwise noted, the terms "modulate," "modulation," "stimulate," and "stimulation" refer generally to signals that have either type of the foregoing effects on the target nerves. Accordingly, a spinal cord "stimulator" can have an inhibitory effect on certain neural populations. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described in the references incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. For example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure.

Figure 1B:
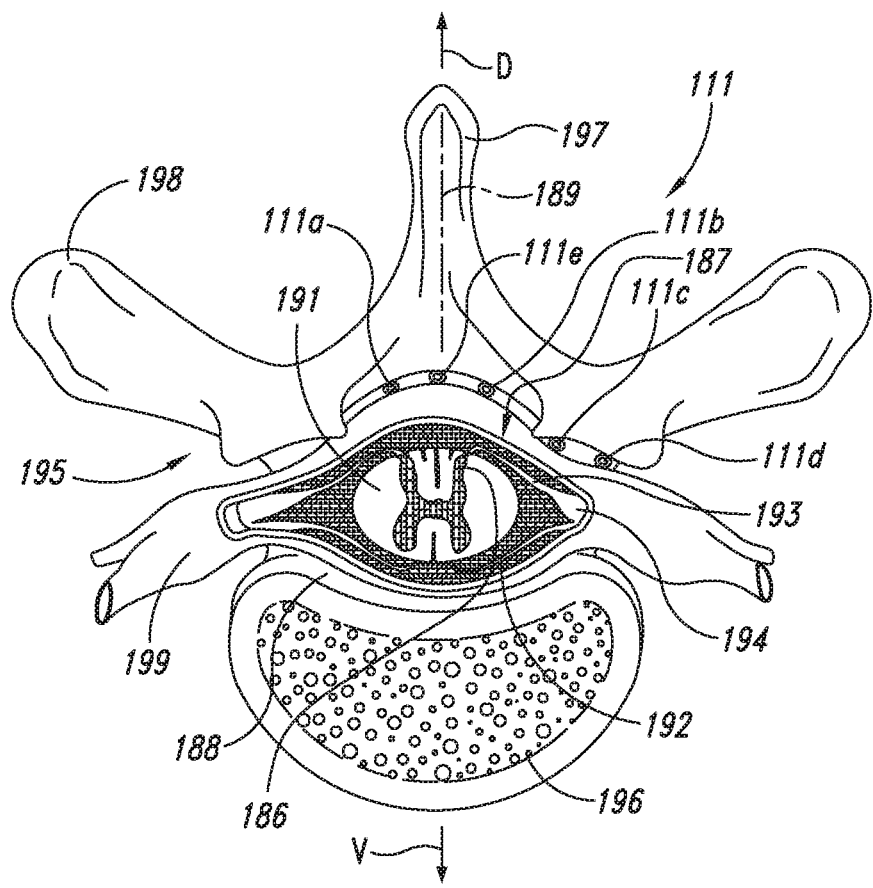
FIG. 1B is a partially schematic, cross-sectional illustration of a patient's spine, illustrating representative locations for implanted lead bodies in accordance with some embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated leads however, leads 111 can be paddle leads. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In some embodiments, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In some embodiments, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e.

In any of the foregoing embodiments, it is important that the signal delivery device 110 and in particular, the therapy or electrical contacts of the device, be placed at a target location that is expected (e.g., by a practitioner) to produce efficacious results in the patient when the device 110 is activated. The following sections describe techniques and systems for simplifying the process of placing contacts via one or more leads 111 which to deliver neural modulation signals to the patient.

2.0 Representative Embodiments

Systems of the type described above with reference to FIGS. 1A-1B can be used to treat patient pain without generating paresthesia, via therapy signals delivered at a frequency between 1.5 kHz and 100 kHz, or between 1.2 kHz and 100 kHz. In addition, systems of the type described above with reference to FIGS. 1A-1B can be used with various therapies using low frequency (LF) that generate paresthesia. The following discussion with reference to FIGS. 2A-6D describes various embodiments of leads having openings disposed within a sidewall of the lead and a lumen extending through a length of the lead to a distal and/or proximal portion of the lead, and are configured to receive a stylet. Compared to leads configured to receive a stylet at a proximal opening, the leads described below with reference to FIGS. 2A-6D can have improved steerability to facilitate more efficient and accurate positioning within a patient, and/or with respect to a pulse generator or other hardware to which the lead may be connected. In some embodiments, the leads can be implantable leads, such as elongated leads or paddle leads. Such leads can be used to deliver any of a variety of suitable electrical signals in addition to or in lieu of signals having a frequency between 1.2 kHz and 100 kHz, such as electrical signals having a frequency between about 5 Hz and 100 Hz, between about 25 Hz and about 75 Hz, and between about 50 Hz and about 100 Hz.

Figure 2A:
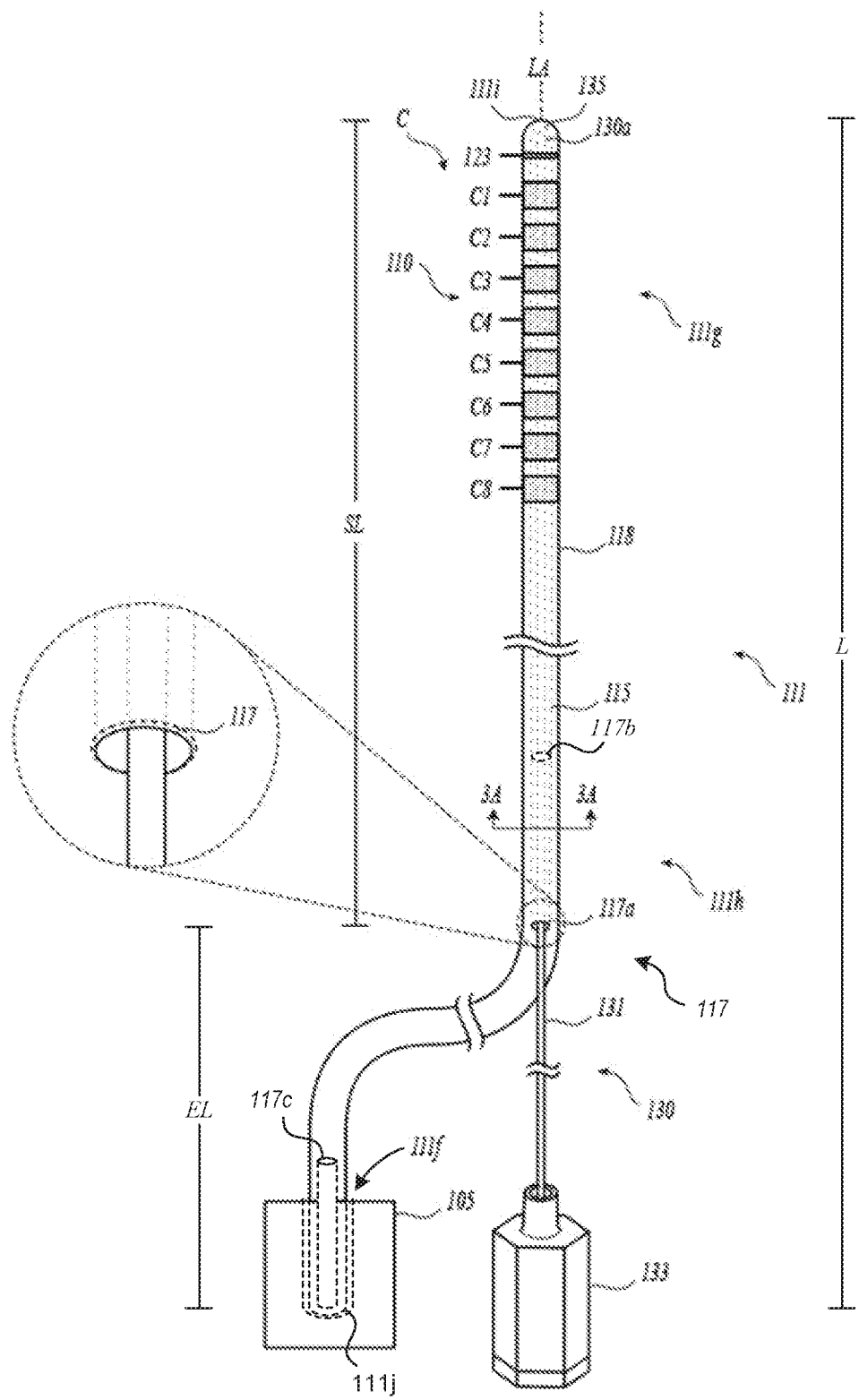
FIG. 2A is a partially schematic side view illustration of a lead configured in accordance with some embodiments of the present technology.
Figure 5:
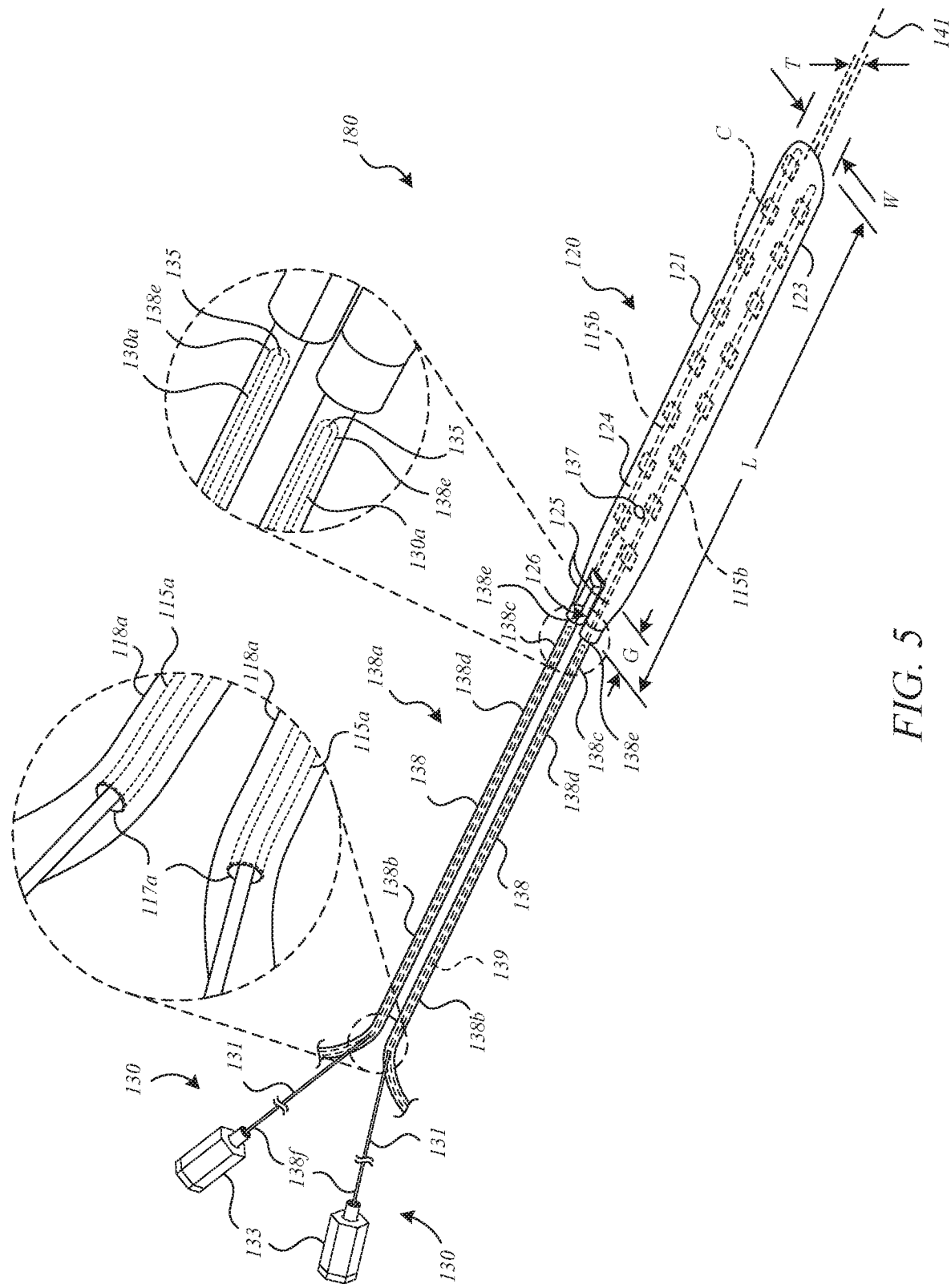
FIG. 5 is a cross-sectional illustration of a lead configured in accordance with some embodiments of the present technology.

FIG. 2A illustrates a side view of a lead 111 having a sidewall 118, an internal lumen 115 positioned inwardly from the sidewall 118, and one or more openings 117 (e.g., ports) disposed within the sidewall 118 to provide a passage to the lumen 115. Leads 111 configured in accordance with the present technology are generally elongated (e.g., having a greater longitudinal dimension than a lateral dimension), and can include paddle leads, as illustrated in FIG. 5. As shown in FIG. 2A, the lead 111 includes a lead body having a proximal portion 111f, a distal portion 111g, and an intermediate portion 111h disposed between the proximal portion 111f and the distal portion 111g. The lead 111 further includes a distal end 111i and a proximal end 111j. The lead lumen 115 can be configured to removably receive at least a portion of a stylet 130 (e.g., a stylet shaft 131) that is sized and shaped to be inserted into the lead lumen 115 through a first opening 117a (e.g., a stylet entry point). Once delivered through the first opening 117a, the stylet shaft 131 is temporarily coupled to the lead 111 to support the lead 111 as it is inserted into the patient at the desired location, and, more specifically, into the patient's epidural space in accordance with some embodiments of the present technology. In other embodiments, the lead can be inserted into the patient's brain or peripheral tissue. The stylet 130 can include a handle 133 that can be fixedly or removably attached to the stylet shaft 131. The handle 133 and the stylet shaft 131 can be made of any number of suitable biocompatible materials. In some embodiments, for example, the handle 133 comprises a thermoplastic such as acrylonitrile butadiene styrene (ABS).

As illustrated in FIG. 2A, when the stylet 130 is inserted into the lead lumen 115, a distal region 130a of the stylet 130 can extend distally through the lumen 115 until a tip 135 of the stylet is positioned proximate to the distal end 111i of the lead 111. The stylet tip 135 can be an atraumatic tip and is thereby restricted/prevented from extending through the distal end 111i of the lead 111. As used herein, and unless otherwise noted, "atraumatic" means causes minimal, if any, injury to a patient's tissue. Alternatively, or in addition to the atraumatic stylet tip 135, when the practitioner moves the stylet 130 through the lead lumen 115 to the distal end 111i, the tip 135 can eventually abut a stylet stop (not shown) located at a terminus of the lead lumen 115, and is therefore unlikely to puncture through the distal end 111i.

In some embodiments, the lead 111 can include more than one opening 117 operably connected to more than one lead lumen 115, each of which can extend distally from each of the openings 117. For example, the lead 111 can include the first opening 117a coupled to a first lead lumen, another opening coupled to a second lead lumen, yet another opening coupled to a third lead lumen, and so on. In some embodiments, each of the openings 117 and lead lumens 115 can be configured to receive the stylet shaft 131 or other elongated shaft configured to support, position, or otherwise facilitate delivery or other handling of the lead 111. In some embodiments, the lead 111 can include more than one opening 117 coupled to a single lead lumen 115, such as two openings (e.g., shown by reference numbers 117a and 117b in FIG. 2A) coupled to the same lead lumen 115, or more than one opening coupled to a first lead lumen and more than one opening coupled to a second lead lumen. Accordingly, the practitioner can pick the opening 117 corresponding to the desired stylet-supported length of the lead 111 suitable for a given patient. When configured with more than one opening 117 and, optionally, more than one lead lumen 115, the lead 111 can be coupled to a first elongated stylet shaft in a first lead lumen and a second elongated stylet shaft in a second lead lumen, etc. Alternatively, the stylet shaft 131 can be inserted into the first opening, removed, and inserted into the second opening that is positioned proximally or distally relative to the first opening along the sidewall 118 of the lead 111. In still further embodiments, the lead can include a third opening 117c that provides stylet access from the intermediate portion 111h to the proximal portion 111f, in addition to, or in lieu of, the first opening 117a that provides access from the intermediate portion 111h to the distal portion 111g. As will be described further with reference to FIGS. 6A-6D, the third lead opening 117c can be used to support the proximal portion of lead 111 as it is inserted into the pulse generator 105 and/or other hardware elements, e.g., the lead extension 102 and/or cable assembly 120 described above with reference to FIG. 1A.

Figure 2B:
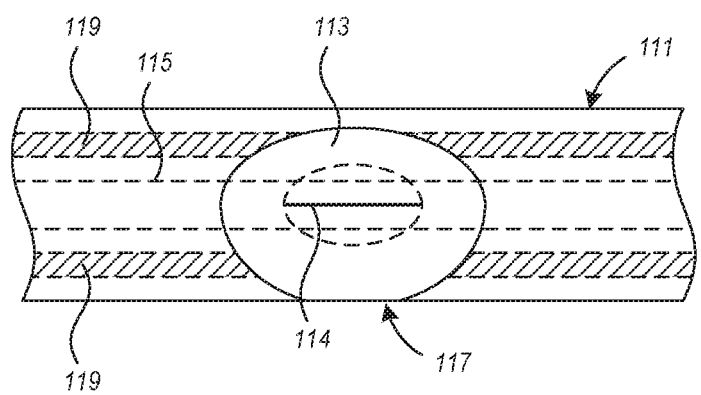
FIG. 2B is a partially schematic side view illustration of a portion of a representative lead having a lumen with an opening and a corresponding seal configured in accordance with embodiments of the present technology.

The lead 111 can further include a membrane that is configured to be penetrated by the stylet shaft 131 and seal at least a portion of a corresponding opening 117 prior to or after engaging the stylet shaft 131. Representative membranes 113 can be plugs or valves (e.g., one-way valves) or continuous structures that can be punctured, torn, or otherwise opened to allow the stylet shaft 131 to enter the lead lumen 115 through the opening 117. In some embodiments, the membrane 113 is a self-sealing septum valve that permits the stylet shaft 131 to pass through, and upon removal of the stylet shaft 131, re-seals to close the lead lumen 115. For example, FIG. 2B illustrates a portion of a representative lead 111 having a lead lumen 115, internal wires 119 that connect to contacts or electrodes (not visible in FIG. 2B), and an opening 117 to provide stylet access into the lead lumen 115. A membrane 113 is positioned over or in the opening 117, and includes a slit 114 that is sized to allow a stylet to be inserted into, and withdrawn from, the opening 117, with the membrane 113 being sufficiently resilient to re-seal the slit 114 when the stylet is withdrawn. In some embodiments, the membrane 113 can be formed from a rigid, semi-rigid, or flexible material to facilitate such sealing, thereby preventing fluid and/or air from entering the lumen 115. In addition, the geometry of the membranes 113 may correspond to that of the openings 117. For example, membranes 113 may have similar cross-sectional geometry as that of the openings 117, to provide proper sealing. The size, diameter, etc. of the membranes 113 may exceed that of the openings 117 by a margin sufficient to facilitate sealing the openings 117.

Referring again to FIG. 2A, in some embodiments, the lead 111 can be elongated along a major or lead axis, such as a longitudinal axis LA. In general, the term "elongated" refers to a physical characteristic of a structure having a length greater than its width. The lead 111 can have an overall lead length L between the distal end 111i and the proximal end 111j that is longer than that of typical leads. For example, the lead length L can be sufficient to position one or more of the signal delivery elements 110 at one or more vertebral locations (including associated neural populations) described herein. For example, the contacts C1-C8 may be positioned at vertebral levels T9-T12 to treat low back pain. Representative lead lengths L are from about 30 cm to about 150 cm, and in some embodiments, from about 40 cm to about 50 cm. As used herein, "about" means within ±10% of the stated value, unless otherwise noted. To accommodate patients having different physical characteristics, leads of the present disclosure can have a lead length L of about 40 cm, about 45 cm, about 50 cm, about 55 cm, about 60 cm, about 65 cm, about 70 cm, about 75 cm, about 80 cm, about 85 cm, about 90 cm, about 95 cm, or about 100 cm.

As described above, the lead lumen 115 extends between the first opening 117a and the distal portion 111g of the lead 111. In some embodiments, the lead lumen 115 extends all the way to (but not through) the distal end 111i rather than only partially within the distal portion 111g. To increase the steerability of the lead 111 compared to other leads, the first opening 117a can be positioned within the sidewall 118 of the intermediate portion 111h of the lead 111. A steerable lead length SL is defined by a longitudinal length of the lead lumen 115 that is accessible to a stylet via an opening. The steerable length SL is typically less than the overall length L of the lead. In this way, rather than steering the entire lead length L of the lead 111 through a lead lumen 115 extending the entire lead length, a practitioner inserts the stylet shaft 131 and actively steers just the steerable lead length SL. The rest of the lead 111 follows. This can increase the practitioner's efficiency and accuracy when positioning the lead 111 within the patient at a treatment site, compared to leads having lumens extending generally into proximal portions of the leads and coupled to proximal openings configured to receive stylets.

Leads in accordance with some embodiments of the present technology can have a steerable length of about 20 cm, about 25 cm, about 30 cm, about 35 cm, about 40 cm, about 45 cm, or about 50 cm, depending on the length of the lead. For example, a representative lead can have a length of 50 cm and a steerable length of 30 cm. Other combinations of lengths and steerable lengths can be selected based on one or more of the patient's physical characteristics. In addition, the lead 111 can include one or more markers (not shown) with each marker indicating a length interval. For example, leads can include markers positioned longitudinally along the steerable length SL and/or lead length L at intervals of 10 cm, such as a lead 111 having an 80 cm length with seven markers spaced 10 cm apart. Practitioners can refer to these markers as the lead 111 is being delivered to, and positioned within, the patient to provide feedback to the practitioner as to what length of the lead 111 has been delivered to the patient.

In some embodiments, the lead 111 can be formed of a single biocompatible material. In some embodiments, the lead 111 can be formed of more than one biocompatible material. For example, more than one biocompatible material can be used over the entire length L of the lead 111, such as a first material forming a first layer, a second material forming a second layer, and so on. In addition to or in lieu of this arrangement, the distal portion 111g of the lead 111 can be formed of a first material, the intermediate portion 111h can be formed of a second material, and the proximal portion 111g can be formed of a third material. Each of these portions can further include layers formed of the same material or a different material. In some embodiments, the distal portion 111g of the lead 111 can be formed of a similar or the same material(s) as the intermediate portion 111h of the lead 111. The material(s) can be selected to form certain portions of the lead 111, and/or to form certain layers of the lead 111, and/or to prevent the stylet 130 from puncturing a portion of the lead 111 as the distal region 130a of the stylet shaft 131 is being delivered to and through the opening 117.

Regardless of the material(s) forming the lead 111, the materials can have different stiffnesses. As such, leads configured in accordance with the present disclosure can be formed of any number of suitable biocompatible materials (e.g., polyurethane and/or silicone, with or without heat treatment and/or other strengthening/reinforcement agents) having a plurality of different stiffnesses. Stiffness, as used herein, refers to a resistance of a material (of the lead) to bending away from the longitudinal axis L of the lead 111. In this way, one or more material(s) can be selected to form a lead 111 having one or more desired stiffnesses along a length L of the lead 111. For example, the distal portion 111g of the lead 111 and the intermediate portion 111h of the lead 111 together can have a first stiffness and the proximal portion 111g of the lead 111 can have a second, different (e.g., greater) stiffness. In some embodiments, the distal portion 111g of the lead 111 can have a third stiffness, the intermediate portion 111h of the lead 111 can have a fourth stiffness, and the proximal portion 111g of the lead 111 can have a fifth stiffness. Similar to the first stiffness and the second stiffness, the third, fourth, and fifth stiffnesses can be generally similar or different. For example, the fifth stiffness can be stiffer than the fourth stiffness which can be stiffer than the third stiffness.

The stiffnesses of the portions of the lead 111 can be generally similar or different. For example, the second stiffness of the proximal portion 111g of the lead 111 can be greater than the first stiffness of the distal portion 111g of the lead 111 and the intermediate portion 111h of the lead 111. In this configuration, the distal portion 111g of the lead 111 and the intermediate portion 111h of the lead 111 comprise the steerable length SL, and the proximal portion 111f comprises an external length EL of the lead 111. As such, the stiffness of the external length EL is greater than the stiffness of the steerable lead length SL. Moreover, when configured to have the first stiffness and the second stiffness, a transition point or region between the first stiffness and the second stiffness can be formed and is often positioned at or near the first opening 117a.

The lead 111 terminates at the distal end 111i which can be made of the same material as the rest of the lead 111, the same as a material used to form a portion of the lead 111, or can be made of a separate material or component. In some embodiments, the distal end 111i can include a radiopaque portion 123 made of, for example, titanium dioxide or barium sulfate, to aid in positioning the lead 111 via fluoroscopy or another suitable visualization technique.

In some embodiments, the stylet shaft 131, or a portion of the stylet shaft, has a stiffness greater than a stiffness of the lead 111 in which it is inserted. In some embodiments, at least a portion of the stylet shaft 131 can be coated with a layer of polytetrafluoroethylene (PTFE) or another suitable fluoropolymer.

The lead 111 can have a plurality of signal delivery elements 110 (e.g., contacts C1-C8) carried by the distal portion 111h of the lead 111 and can be positioned to deliver modulation signals in accordance with some embodiments of the disclosure. The signal delivery elements 110 are accordingly positioned to contact the patient's tissue when implanted. The contacts C can be ring-shaped and/or can have other shapes. The lead 111 includes internal wires or conductors (described further below with reference to FIGS. 3A-3D) that extend between the proximal end 111j of contacts C at or near the distal region 111g of the lead 111. The contacts C can be made of any suitable biocompatible metal such as titanium, a noble metal such as platinum or iridium, or alloys thereof. In some embodiments, the contacts C can be coated with materials to improve contact performance or increase the surface area of the contacts C. These materials can include, for example, platinum black, titanium nitride, iridium oxide, or other materials having generally similar material properties. After implantation, the connection contacts C are connected to the external programmer 105 or to the implanted pulse generator 101 discussed above with reference to FIG. 1A.

The lead 111 can be introduced into the patient via a needle, catheter, or the like. In use, the practitioner inserts the stylet shaft 131 into the lead lumen 115, which generally straightens the distal portion 111g of the lead 111 and the intermediate portion 111h of the lead for implantation. Together, the distal region 130a of the stylet 130 and the distal portion 111g of the lead 111 form a distal zone which can be generally straight, optionally with a curved tip (not shown) to aid in steering the lead. Prior to implantation, the shaft 131 of the stylet 130 or other delivery device is slideably and releasably inserted (via the handle 133) into an axially-extending opening (lead lumen 115) in the lead 111 via the opening 117. Once inserted, the shaft 131 extends distally through the lumen 115 along the steerable length SL of the lead 111. During implantation, the lead 111 is positioned in a catheter (not shown) which is inserted into the patient's body. The lead 111 can then be deployed from the catheter using the stylet 130, which supports the lead 111 as the stylet 130 and the lead 111 are moved together until the distal portion 111g and the associated contacts C1-C8 are at the desired location (e.g., treatment site) in the patient. The shaft 131 can generally be flexible, but more rigid than the lead 111, to allow the practitioner to insert the lead 111 and control its position. The lead 111 can be anchored in place once the distal portion 111g is positioned at or near the treatment site. As discussed later, with reference to FIG. 4, suitable anchors can be attached to adjacent ligaments, bone, and/or other structures.

After positioning the lead 111, the stylet shaft 131 can be readily and freely removed from the lead lumen 115 by withdrawing the distal end 130a of the stylet shaft 131 away from the spinal cord modulation site and extracting the stylet shaft 131 from the lead lumen 115. In some embodiments, at least one of an inner surface of the lead lumen 115 and an outer surface of the stylet shaft 131 can include a material positioned to facilitate relative sliding and free separation between the surfaces. For example, a PTFE liner or the coating can be placed on an inner surface of the lead lumen 115, in addition to or in lieu of placing it on the stylet shaft 131. Upon removal, at least the distal portion 111g of the lead 111 remains generally straight at the desired treatment location. In some embodiments, a portion of the intermediate portion 111h can also remain generally straight.

Figure 3A:
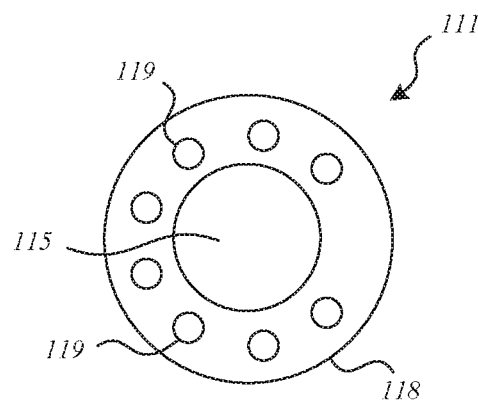
FIG. 3A is a partially schematic cross-sectional illustration of the lead of FIG. 2A taken generally along line 3A-3A.
Figure 3B:
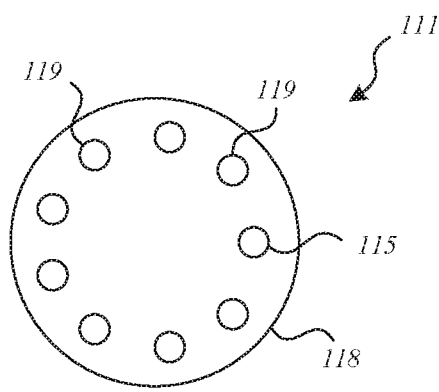
FIGS. 3B-3D are partially schematic cross-sectional illustrations of other leads configured in accordance with some embodiments of the present technology.
Figure 3C:
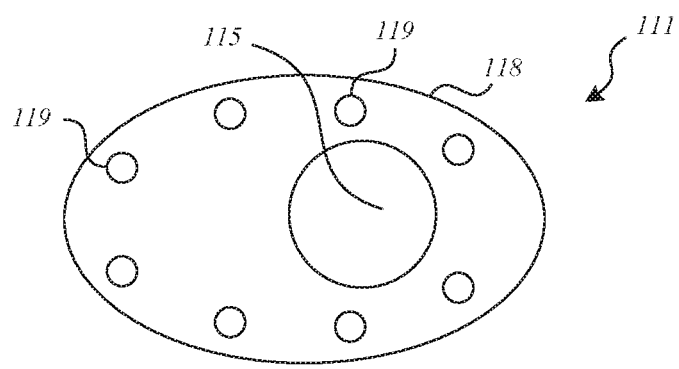
Figure 3D:
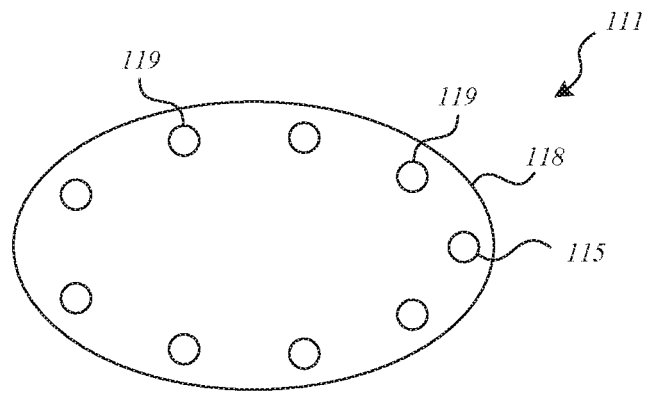

FIG. 3A is a cross-sectional illustration of a representative lead 111 having a circular cross-sectional shape, taken generally along line 3A-3A of FIG. 2A. One or more internal wires 119 can electrically connect the contacts C1-C8 (FIG. 2A) to other features of the systems described herein with reference to FIG. 1A, such as the external programmer 105. In the illustrated embodiment, the internal wires 119 are housed in corresponding wire lumens that extend longitudinally along the length of the lead 111 and are positioned adjacent to the sidewall 118. In general, the lead lumen 115 is positioned in a generally central portion of the lead 111 with respect to the longitudinal axis LA. In some embodiments, the lead 111 can also have an elliptical cross-section as illustrated in FIG. 3C, rather than the generally circular cross-section illustrated in FIG. 3A. In addition, as illustrated in FIG. 3B and FIG. 3D, the lead lumen 115 can be positioned adjacent to the sidewall 118 along with the internal wires 119 rather than in the generally central portion of the lead 111 shown in FIGS. 3A and 3C.

Figure 4:
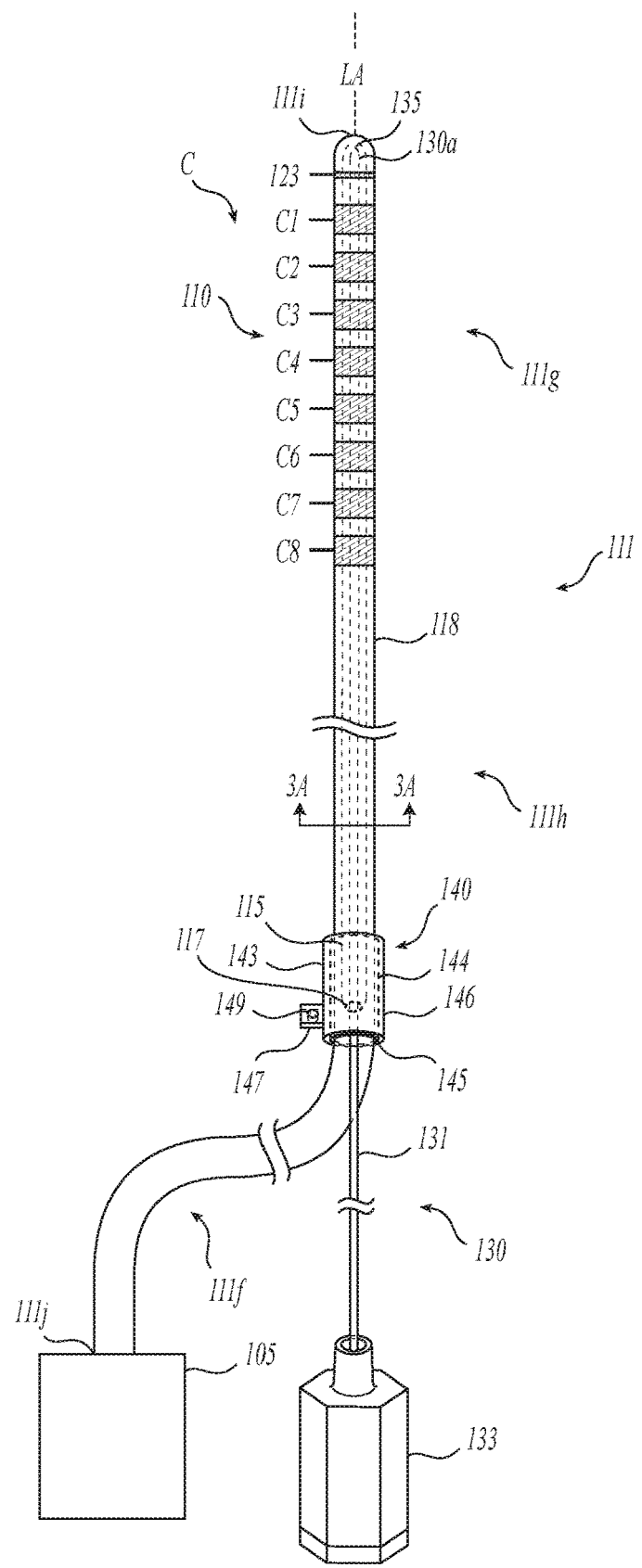
FIG. 4 is a partially schematic side view illustration of a lead configured in accordance with some embodiments of the present technology.

Referring next to FIG. 4, the lead 111 can further include a lead anchor 140, which releasably carries the lead 111 and can anchor the lead 111 in a position relative to the patient's tissue. For example, when the distal portion 111g is positioned at the treatment site, the practitioner can secure the intermediate portion 111h relative to the patient with the lead anchor 140 and can partially or completely remove the stylet 130 from the lead lumen 115 through the sidewall opening 117. Lead anchors 140 useful with leads of the present technology can have an anchor stiffness greater than any lead stiffness and can prevent the stylet from extending outwardly from the lead body. For example, when the lead anchor 140 is positioned around a portion of the sidewall 118 carrying the opening 117, the anchor 140 can provide added stiffness to the portion of the sidewall 118 thereby preventing the portion of the sidewall 118 from being penetrated and/or perforated by the stylet tip 130a.

The lead anchor 140 can include a longitudinally-extending anchor body 143 having a longitudinally extending aperture 145 that receives the lead 111. The anchor body 143 includes a sleeve 144 in which the longitudinally extending aperture 145 is positioned. The aperture 145 is sized and configured to receive the lead 111 therethrough. A retainer 146 is disposed around the sleeve 144 and is operable to compress or constrict at least a portion of the sleeve 144 against the lead 111 extending through the sleeve 144. The lead 111 is accordingly retained in position relative to the anchor 140 by friction developed between the sleeve 144 and lead 111 due to the compression force exerted by the retainer 146. In general, the circumferential extent of the retainer 146 is sufficient to capture and/or compress the lead 111 in a generally uniform manner. The sleeve 144 and the retainer 146 can be formed from any biocompatible material suitable to exert sufficient compression force to retain the lead 111 in position within longitudinally extending aperture 145, e.g., as disclosed in U.S. Patent Application Publication No. 2015/0005859, which is incorporated herein by reference in its entirety.

The lead anchor 140 can further comprise one or more anchor tabs 147 extend laterally from the anchor body 143 e.g., on opposite sides. Each anchor tab 147 can include an aperture 149 or other feature to facilitate attaching the lead anchor 140 to a patient's tissue.

In some embodiments, the lead anchor 140 can be configured to mate with the lead using any number of suitable lead anchor 140 mating features (not shown), such as through an opening, a groove, a slit, a channel, or the like, to receive the lead body. In some embodiments, the lead anchor 140 can be used to help seal the opening 117 into the lead lumen 115. Accordingly, the lead 111 can have pre-set anchor locations near (or coincident with) the opening 117.

In a representative embodiment illustrated in FIG. 5, the lead is a paddle lead 180 and includes a paddle body 120 elongated along a longitudinal axis 141. The paddle body 120 has a length L along the longitudinal axis 141, a width W transverse to the longitudinal axis 141, and a thickness T transverse to the width W. In general, the paddle body 120 has a flattened configuration, with the thickness T less than the width W and the length L. The paddle body 120 can have a first or upper surface 122 and a second or lower surface 123. The paddle body 120 carries one or more contacts C that are accessible from the lower surface 121. Accordingly, when the paddle body 120 is implanted, the contacts C at the lower surface 133 are positioned to direct electrical signals toward the target location, e.g., the spinal cord.

Electrical current is directed to the paddle body 120 via one or more lead tails 138, each of which carries one or more conductors 139 (shown schematically in FIG. 5). For example, the paddle body 120 can carry 16 contacts C, which are supplied with electrical current by a corresponding set of sixteen conductors 139, eight of which are housed in one lead tail 138, and the remaining eight of which are housed in the other lead tail 138. The lead tails 138 connect to the paddle body 120 at corresponding lead legs 125. The lead legs 125 can be separated by a gap 126 having a longitudinal dimension G generally aligned with the longitudinal axis 141. Additional features of the paddle lead 180 are disclosed in U.S. Patent Application Publication No. 2018/0256892, which was previously incorporated herein by reference in its entirety.

Similar to the lead 111 of FIG. 2A, the lead tails 138 illustrated in FIG. 5 can each include a lead tail sidewall 118a, an internal lead tail lumen 115a positioned inwardly from the lead tail sidewall 118a, and a lead tail opening 117a disposed within the lead tail sidewall 118a to provide a passage to the lead tail lumen 115a. The lead tails 138 each include a lead tail body 138a having a lead tail proximal portion 138b, a lead tail distal portion 138c, and a lead tail intermediate portion 138d disposed between the lead tail proximal portion 138b and the lead tail distal portion 138c. The lead tails 138 further include a lead tail distal end 138e and a lead tail proximal end 138f. The lead tail lumen 115a can be configured to removably receive at least a portion of a stylet 130 (e.g., a stylet shaft 131) that is sized and shaped to be inserted into the lead tail lumen 115a through the lead tail opening 117a. When the stylet 130 is inserted into the lead tail lumen 115a, a distal region 130a of the stylet 130 can extend distally through the lead tail lumen 115a until a tip 135 of the stylet is positioned proximate to the lead tail distal end 138e of the lead tail 138. Unless stated otherwise, the lead tails 138 of FIG. 5 behave similarly to lead 111 described above and illustrated in FIG. 2A. For example, when the practitioner inserts the stylet shaft 131 into the lead tail lumen 115a, the inserted stylet shaft 131 generally straightens the lead tail distal portion 138c and the lead tail intermediate portion 138d for implantation. In another embodiment, the paddle lead 180 can be delivered into the patient using one stylet 130. The stylet 130 can be introduced into the paddle body 120 itself, such as into a paddle lumen (not shown) through a paddle opening 137 operatively connected to the paddle lumen (not shown). In this embodiment, the paddle body 120 can be steered in a similar manner as described above with respect to the lead tails 138 and the leads 111.

As described above, the distal portion 138c corresponds to the distal portion of the lead tail 138. Accordingly, the lead tail lumen 115a extends through the distal portion 138c to the end of the distal portion 138c. Alternatively, the lead tail 138 and the paddle body 120 can be considered together, with the paddle body 120 forming the distal portion of the overall lead 180. Accordingly, the lead tail lumen 115a extends to but not through the distal portion. To provide greater control over the paddle lead 180, the lead lumen can extend to and through the distal portion (e.g., paddle body 120) to the end of the paddle body 120, as indicated by reference numeral 115b. Accordingly, in some embodiments, the lead lumen extends to the distal portion of the lead, or into the distal portion of the lead, or entirely through the distal portion of the lead to the end of the distal portion (but not so far as to puncture through the distal end of the lead).

With any of the foregoing leads and associated systems, it is important for the practitioner to accurately position the lead in order to provide effective therapy. With varying patient anatomies and tight spaces in which to navigate, practitioners often must position and re-position the lead during implantation in order to accurately place the lead at a target treatment site. Compared to shorter leads, leads having longer lengths are more difficult for practitioners to steer during positioning, which can increase the duration of an implantation procedure or reduce accuracy of lead placement. For example, the greater length of the lead adds uncertainty about the correlation between a given movement or action by the practitioner at the proximal end of the lead, and the resulting movement or action of the lead at the distal end. This applies to linear motions (lateral and/or axial) and rotational motions. More specifically, the stylet may have a curved tip. By rotating the stylet, the practitioner can change the direction in which the curved tip points, and therefore, the direction in which the lead travels. For long leads, the practitioner's rotation of the stylet at the proximal end may not correspond to a similar rotation at the distal end because the stylet is at least somewhat torsionally flexible—and over greater lead lengths, the torsional flexibility produces a greater disparity between the amount of stylet rotation at the proximal end and the corresponding rotation of the distal end of the stylet. In still another example, the stylet may buckle when an axial force is applied to it over a great distance. Accordingly, the process of placing the lead can be difficult. As a result, there exists a need for a lead which provides for precise navigation regardless of the lead length. As discussed herein, embodiments of the present technology include leads having various lead lengths L yet can be steered by a practitioner as though each of the leads have generally similar lead lengths L, e.g., because the different leads have steerable lengths SL that are similar or the same. Accordingly, a practitioner who becomes proficient at steering a lead with a given total length and steerable length can apply that proficiency to a lead having a different total length, but the same steerable length.

Several of the embodiments described above were described in the context of sidewall openings that facilitate improved handling of the distal end of the lead. In addition to, or in lieu of, improving handling of the distal portion, sidewall openings can improve the practitioner's ability to handle the proximal portion of the lead. Representative embodiments of such sidewall openings are described further below with reference to FIGS. 6A-6D.

Figure 6A:
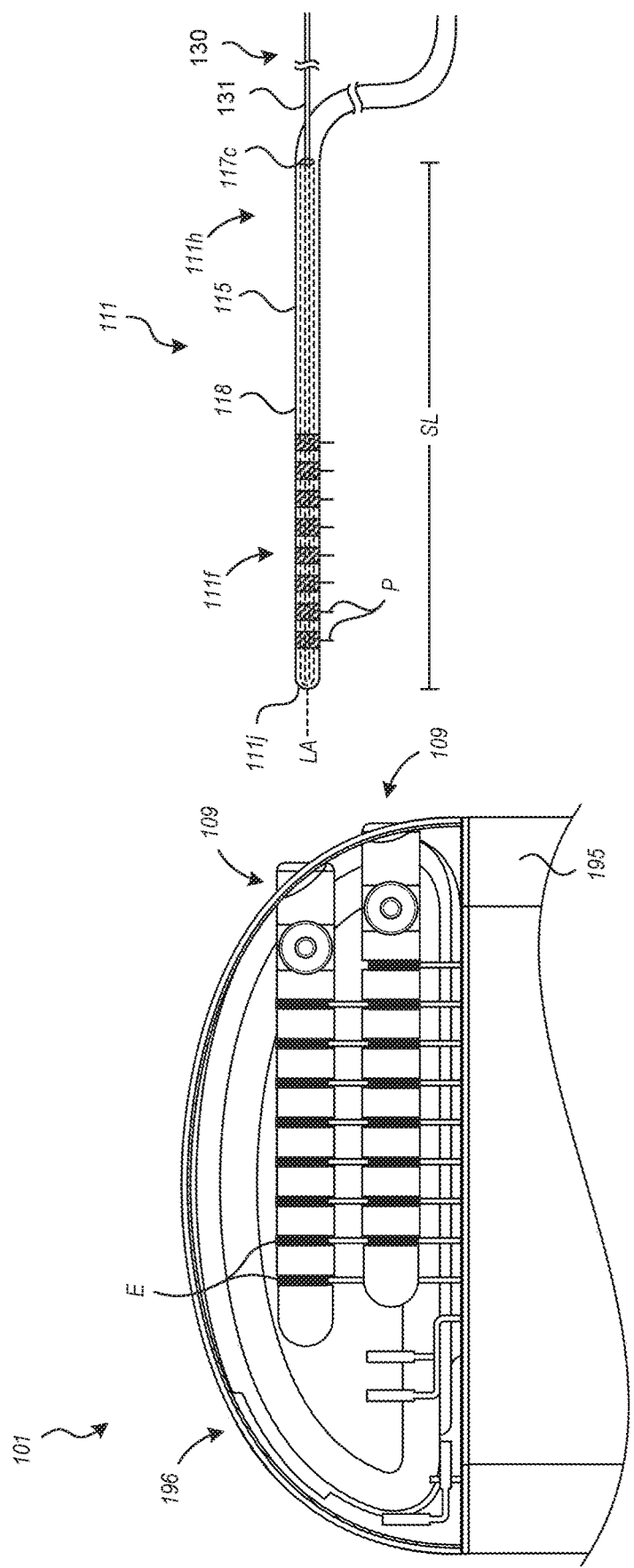
FIGS. 6A-6D are partially schematic illustrations of lead proximal portions having lumens accessible via openings for one or more stylets, in accordance with embodiments of the present technology.

FIG. 6A is a partially schematic illustration of a representative signal generator 101 and the proximal portion 111*f* of a corresponding lead 111. The signal generator 101 includes a body or can 195 in which the processor, battery, and/or other electronic components are typically housed. The signal generator 101 can also include a header 196 that is configured to connect the internal electronics to the lead 111. In a representative embodiment shown in FIG. 6A, the header 196 includes two receiving elements 109, each configured to receive a corresponding lead 111. Each of the receiving elements 109 includes header contacts E positioned to align with, and electrically contact, corresponding proximal contacts P carried by the lead 111. The proximal contacts P are electrically connected to the distal contacts C (shown in FIG. 2A) with corresponding conductors 119 (shown in FIGS. 3A-3D). The intermediate portion 111*h* of the lead 111 can include a third opening 117*c* that provides access to the lumen 115 for a stylet 130. The stylet 130 can be inserted into the third opening 117*c* until the end of the stylet 130 is positioned at or close to the proximal end 111*j* of the lead 111. In this manner, the practitioner can temporarily support the proximal portion 111*f* of the lead 111 as the lead is being inserted into the corresponding receiving element 109 of the signal generator 101. The additional stiffness provided by the stylet 130 can make it easier for the practitioner to insert the lead 111 into the receiving element 109. After the lead 111 has been successfully inserted into the receiving element 109, the practitioner withdraws the stylet 130.

One feature of the foregoing arrangement described above with reference to FIG. 6A is that the lead 111 is only temporarily supported by the stylet 130 during the time it takes to successfully insert the lead 111 into the signal generator 101. This approach avoids the need to insert epoxy or another stiffening agent into the stylet lumen 115. In addition to reducing the number of manufacturing steps required to produce the lead, eliminating the need to permanently stiffen the proximal portion 111*f* of the lead 111 reduces the likelihood for a stiffened portion of the lead to project outwardly from the signal generator 101, which can be uncomfortable for the patient. Instead, after the stylet 130 has been removed, the entire proximal portion 111*f* of the lead that extends out from the signal generator 101 is relatively flexible, and is therefore less likely to create discomfort for the patient.

Figure 6D:
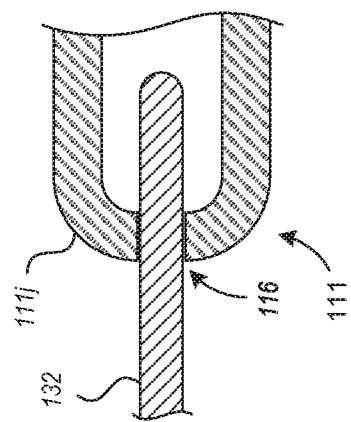
Figure 6C:
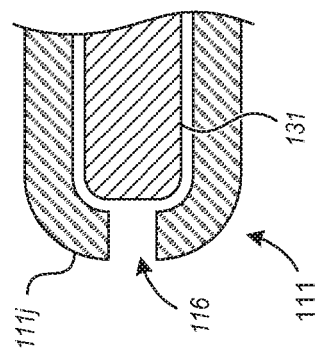
Figure 6B:
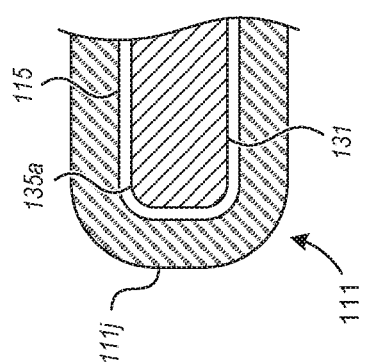

The proximal end 111*j* of the lead 111 can have a variety of different configurations. For example, referring first to FIG. 6B, the proximal end 111*j* can be closed so as to provide full support for the proximal tip 135*a* of the stylet shaft 131. In another embodiment, shown schematically in FIGS. 6C and 6D, the proximal end 111*j* of the lead 111 can include an end opening 116. The end opening 116 is small enough that the stylet shaft 131 will not extend through it. The end opening 116 is large enough to accommodate a smaller, second stylet 132, as shown in FIG. 6D. The second stylet 132 can be inserted from the proximal end toward the distal end, if needed for steering during lead insertion, and/or for making subsequent adjustments to the position of the lead, and/or for extracting the lead.

From the foregoing, it will be appreciated that some embodiments of the presently disclosed technology have been described herein for purposes of illustration, but various modifications may be made without deviating from the disclosed technology. For example, the leads and lead lumens can have lengths and/or shapes that differ from those specifically described above. In addition, the leads can include one or more openings positioned at a number of different locations in the distal portion and/or the intermediate portion of the leads. For leads having stylet access to both the distal and proximal ends of the lead, that access can be provided via a single lumen that extends from the proximal end to the distal end, or two lumens, one extending from the intermediate portion of the proximal end, and one extending from the intermediate portion to the distal end.

Certain aspects of the technology described in the context of some embodiments may be combined or eliminated in some embodiments. For example, in some embodiments, the lead and stylet can comprise a device, a system, or portions thereof. Furthermore, leads can be coupled to the stylets prior to inserting the lead into the delivery device (e.g., catheter) and can be provided to a practitioner as a set including the lead and the stylet. Additionally, the stylets disclosed herein can be used with leads having shapes or designs other than those specifically described above.

While advantages associated with some embodiments of the disclosed technology have been described in the context of those embodiments, not all embodiments need necessarily exhibit such advantages to fall within the scope of the present technology. To the extent that any of the foregoing patents, published applications, and/or other materials incorporated herein by reference conflict with the present disclosure, the present disclosure controls.

The following examples are provided to further illustrate embodiments of the present technology and are not to be interpreted as limiting the scope of the present technology. To the extent that certain embodiments or features thereof are mentioned, it is merely for purposes of illustration and, unless otherwise specified, is not intended to limit the present technology. One skilled in the art may develop equivalent means without the exercise of inventive capacity and without departing from the scope of the present technology. It will be understood that many variations can be made in the procedures herein described while still remaining within the bounds of the present technology. Such variations are intended to be included within the scope of the presently disclosed technology. As such, embodiments of the presently disclosed technology are described in the following representative examples.

1. A patient therapy device, comprising:
   a patient-implantable lead having a proximal portion, an intermediate portion and a distal portion, at least one electrical contact disposed at at least one of the distal portion or the proximal portion, and a lumen inside of the lead, wherein the lumen extends from at least one of a distal end or a proximal end of the lead at least to an opening disposed within a sidewall of the intermediate portion; and
   a stylet having a shaft with a proximal region and a distal region, wherein the distal region of the stylet is sized and shaped to be removably inserted into the lumen through the opening.

2. The patient therapy device of clause 1, wherein the distal region and the distal portion together comprise a distal zone of the device.

3. The patient therapy device of clause 2, wherein the distal zone of the device is generally straight.

4. The patient therapy device of any of the foregoing clauses, wherein the distal portion of the lead is generally straight in a deployed configuration.

5. The patient therapy device of any of the foregoing clauses, wherein the lead has a lead length measured from the proximal end of the lead to the distal end of the lead.

6. The patient therapy device of clause 5, wherein the lead length is selected from the group consisting of about 50 centimeters (cm), about 55 cm, about 60 cm, about 65 cm, about 70 cm, about 75 cm, about 80 cm, about 85 cm, about 90 cm, about 95 cm, and about 100 cm.

7. The patient therapy device of clause 6, wherein the lead has a steerable length extending from the opening to the distal end of the lead.

8. The patient therapy device of clause 7, wherein the steerable length is selected from the group consisting of about 10 cm, about 15 cm, about 20 cm, about 25 cm, about 30 cm, about 35 cm, about 40 cm, about 45 cm, and about 50 cm.

9. The patient therapy device of clause 8, wherein the lead has a lead length selected from the group consisting of about 50 cm, about 60 cm, and about 70 cm, and the lead has a steerable length of about 30 cm.

10. The patient therapy device of clause 1, wherein the lead has a steerable length extending from the opening to the proximal end of the lead.

11. The patient therapy device of clause 10, wherein the steerable length from about 1 cm to about 10 cm.

12. The patient therapy device of clause 11, wherein the steerable length is about 2.5 cm.

13. The patient therapy device of any of the foregoing clauses, wherein the lead is a first lead having a first lead length and a first steerable length extending from the opening of the first lead to the distal end of the first lead and wherein the therapy device further comprises a second lead having a second lead length different than the first lead length, and a second steerable lead length at least approximately the same as the first steerable lead length.

14. The patient therapy device of clause 13, further comprising a third lead having a third lead length different than the first and second lead lengths, and a third steerable lead length at least approximately the same as the first steerable lead length.

15. The patient therapy device of any of the foregoing clauses, wherein the lumen extends longitudinally along a longitudinal axis of the lead between the opening and the at least one of the distal end or the proximal end, and is positioned centrally in the lead, when viewed in a cross-section normal to the longitudinal axis of the lead.

16. The patient therapy device of any of the foregoing clauses, wherein the lumen extends longitudinally along a longitudinal axis of the lead between the opening and the at least one of the distal end or the proximal end, and is positioned off-center in the lead, when viewed in a cross-section normal to the longitudinal axis of the lead.

17. The patient therapy device of any of the foregoing clauses, wherein the intermediate portion of the lead and the at least one of the distal portion or the proximal portion of the lead have a generally circular cross-sectional shape.

18. The patient therapy device of any of the foregoing clauses, wherein the intermediate portion of the lead and the at least one of the distal portion or the proximal portion of the lead have an elliptical cross-sectional shape.

19. The patient therapy device of any of the foregoing clauses, wherein the distal portion and the intermediate portion together have a first stiffness and the proximal portion has a second stiffness greater than the first stiffness.

20. The patient therapy device of any of the foregoing clauses, further comprising a lead anchor coupleable to the lead.

21. The patient therapy device of clause 20, wherein the lead anchor further comprises:

a longitudinally extending sleeve having an aperture sized and positioned to receive the lead; and
a retainer disposed around the sleeve and operable to compress at least a portion of the sleeve against the lead.

22. The patient therapy device of clause 21, wherein the lead anchor further comprises at least one anchor tab positioned to facilitate attaching the lead anchor to a patient.

23. The patient therapy device of clause 21, wherein the anchor is positioned to engage the intermediate portion of the lead comprising the opening.

24. The patient therapy device of clause 20, wherein the anchor has a stiffness greater than a stiffness of the proximal portion of the lead.

25. The patient therapy device of any of the foregoing clauses, wherein the opening is a first opening and wherein the lead has a second opening disposed in the sidewall of the intermediate portion, the first opening being positioned between the second opening and the distal portion.

26. A spinal cord modulation lead for positioning within a patient and delivering electrical modulation signals to the patient at a treatment site, the lead comprising:
at least one electrical contact; and
a lead body having;
  a proximal portion,
  a distal portion, wherein the at least one electrical contact is disposed at the distal portion,
  an intermediate portion disposed between the proximal portion and the distal portion,
  a distal end, wherein the distal end is atraumatic
  a sidewall extending longitudinally along a longitudinal axis of the lead body,
  the sidewall having an opening at the intermediate portion, and
  a lumen positioned interiorly from the sidewall and extending longitudinally between the distal end and the opening.

27. The lead of clause 26, wherein the opening is sized and shaped to receive a stylet removably insertable into the lumen through the opening.

28. The lead of clause 27, further comprising a membrane penetrable by the stylet and positioned over or within the opening.

29. The lead of clause 28, wherein the membrane includes a plug or a valve.

30. The lead of clause 29, wherein the valve includes a one-way valve.

31. The lead of clause 30, wherein the one-way valve includes a septum valve.

32. The lead of clause 26, wherein the distal portion is generally straight when positioned at the treatment site.

33. The lead of any of clauses 26-32, wherein the lead has a lead length extending between a proximal end of the lead and the distal end.

34. The lead of clause 33, wherein the lead length is selected from the group consisting of about 50 centimeters (cm), about 55 cm, about 60 cm, about 65 cm, about 70 cm, about 75 cm, about 80 cm, about 85 cm, about 90 cm, about 95 cm, and about 100 cm.

35. The lead of clause 26, wherein the lead has a steerable length extending between the opening and the distal end of the lead.

36. The lead of clause 35, wherein the steerable length is selected from the group consisting of about 10 cm, about 15 cm, about 20 cm, about 25 cm, about 30 cm, about 35 cm, about 40 cm, about 45 cm, and about 50 cm.

37. The lead of clause 26, wherein the lead has a lead length selected from the group consisting of about 50 cm, about 60 cm, and about 70 cm, and the lead has a steerable length of about 30 cm.

38. The lead of clause 26, wherein the distal portion and the intermediate portion together have a first stiffness and the proximal portion has a second stiffness greater than the first stiffness.

39. The lead of any of clauses 26-38, wherein the at least one contact is a first electrical contact and the opening is a first opening, and wherein the lead further comprises a second electrical contact at the proximal portion, and wherein the lead has a second opening in the sidewall, the second opening being between the first opening and a proximal end of the lead, with the lumen extending proximally from the second opening to the proximal end of the lead.

40. A method for treating a patient, comprising:
  inserting a stylet into an opening within a sidewall of the lead, wherein the opening is located in an intermediate portion of the lead, between a distal end and a proximal end of the lead;
  positioning the lead in a catheter, the lead carrying an electrode;
  deploying the lead from the catheter; and
  withdrawing the stylet from the lead through the opening by moving the stylet proximally away from the distal end of the lead through the lumen while the lead remains at a spinal modulation site.

41. The method of clause 40, wherein positioning the lead further comprises steering a steerable portion of the lead, the steerable portion comprising the intermediate portion and the distal end of the lead.

42. The method of clause 41, wherein deploying the lead further comprises:
  moving the stylet into a lumen extending longitudinally between the opening and the distal end of the lead; and
  positioning the lead with the stylet so that the lead is proximate to a spinal modulation site.

43. The method of clause 42, wherein positioning the lead further comprises moving the steerable portion of the lead relative to a proximal portion of the lead with the stylet.

44. The method of any of clauses 40-43, further comprising preventing the stylet from extending outwardly from a lead body by positioning a lead anchor around a portion of the sidewall carrying the opening.

45. The method of any of clauses 40-44, further comprising delivering electrical modulation signals to the spinal modulation site via the electrode carried by the lead.

46. The method of any of clauses 40-45, further comprising positioning the stylet in the steerable portion of the lead before deploying the lead from the catheter.

47. A method for treating a patient, comprising:
  withdrawing a stylet from a lead through an opening within a sidewall of the lead arranged at an intermediate portion of the lead.

48. The method of clause 47, wherein withdrawing the stylet includes moving the stylet proximally away from a distal end of the lead through a lead lumen while the lead remains at a modulation site.

49. The method of clause 47, wherein withdrawing the stylet includes moving the stylet distally away from a proximal end of the lead through a lead lumen after inserting the proximal end and the stylet into a pulse generator to electrically connect the lead to the pulse generator.

50. The method of clause 47, further comprising:
  inserting the stylet into the opening, wherein the intermediate portion is located between a distal end and a proximal end of the lead;
  positioning the lead in a catheter, the lead carrying an electrode; and
  deploying the lead from the catheter.

51. The method of clause 47, further comprising;
  inserting the stylet into the opening, wherein the intermediate portion is located between a proximal end and a distal end of the lead; and
  inserting the stylet and the proximal end of the lead into a pulse generator.

52. The method of any of clauses 47-51, wherein the lead is an implantable lead.

53. The method of clause 52, wherein the implantable lead is a spinal cord stimulation lead, a deep brain stimulation lead, a peripheral nerve stimulation lead, or a sacral stimulation lead.

We claim:

1. A patient therapy device, comprising:
  a patient-implantable lead having a proximal portion, an intermediate portion and a distal portion, the intermediate portion having a sidewall, the sidewall having an opening extending transverse to a length of the lead, the lead further having at least one electrical contact disposed at at least one of the distal portion or the proximal portion, and a lumen inside of the lead, wherein the lumen extends from at least one of a distal end or a proximal end of the lead at least to the opening; and
  a stylet having a shaft with a proximal region and a distal region, wherein the distal region of the stylet is sized and shaped to be removably inserted into the lumen through the opening.

2. The patient therapy device of claim 1, wherein the distal region and the distal portion together comprise a distal zone of the device.

3. The patient therapy device of claim 2, wherein the distal zone of the device is generally straight.

4. The patient therapy device of claim 1, wherein the distal portion of the lead is generally straight in a deployed configuration.

5. The patient therapy device of claim 1, wherein the lead has a lead length measured from the proximal end of the lead to the distal end of the lead.

6. The patient therapy device of claim 5, wherein the lead length is selected from the group consisting of about 50 centimeters (cm), about 55 cm, about 60 cm, about 65 cm, about 70 cm, about 75 cm, about 80 cm, about 85 cm, about 90 cm, about 95 cm, and about 100 cm.

7. The patient therapy device of claim 6, wherein the lead has a steerable length extending from the opening to the distal end of the lead.

8. The patient therapy device of claim 7, wherein the steerable length is selected from the group consisting of about 10 cm, about 15 cm, about 20 cm, about 25 cm, about 30 cm, about 35 cm, about 40 cm, about 45 cm, and about 50 cm.

9. The patient therapy device of claim 8, wherein the lead has a lead length selected from the group consisting of about 50 cm, about 60 cm, and about 70 cm, and the lead has a steerable length of about 30 cm.

10. The patient therapy device of claim 1, wherein the lead has a steerable length extending from the opening to the proximal end of the lead.

11. The patient therapy device of claim 10, wherein the steerable length from about 1 cm to about 10 cm.

12. The patient therapy device of claim 11, wherein the steerable length is about 2.5 cm.

13. The patient therapy device of claim 1, wherein the lead is a first lead having a first lead length and a first steerable length extending from the opening of the first lead to the distal end of the first lead and wherein the therapy device further comprises a second lead having a second lead length different than the first lead length, and a second steerable lead length at least approximately the same as the first steerable lead length.

14. The patient therapy device of claim 13, further comprising a third lead having a third lead length different than the first and second lead lengths, and a third steerable lead length at least approximately the same as the first steerable lead length.

15. The patient therapy device of claim 1, wherein the lumen extends longitudinally along a longitudinal axis of the lead between the opening and the at least one of the distal end or the proximal end, and is positioned centrally in the lead, when viewed in a cross-section normal to the longitudinal axis of the lead.

16. The patient therapy device of claim 1, wherein the lumen extends longitudinally along a longitudinal axis of the lead between the opening and the at least one of the distal end or the proximal end, and is positioned off-center in the lead, when viewed in a cross-section normal to the longitudinal axis of the lead.

17. The patient therapy device of claim 1, wherein the intermediate portion of the lead and the at least one of the distal portion or the proximal portion of the lead have a generally circular cross-sectional shape.

18. The patient therapy device of claim 1, wherein the intermediate portion of the lead and the at least one of the distal portion or the proximal portion of the lead have an elliptical cross-sectional shape.

19. The patient therapy device of claim 1, wherein the distal portion and the intermediate portion together have a first stiffness and the proximal portion has a second stiffness greater than the first stiffness.

20. The patient therapy device of claim 1, further comprising a lead anchor coupleable to the lead.

21. The patient therapy device of claim 20, wherein the lead anchor further comprises:
a longitudinally extending sleeve having an aperture sized and positioned to receive the lead; and
a retainer disposed around the sleeve and operable to compress at least a portion of the sleeve against the lead.

22. The patient therapy device of claim 21, wherein the lead anchor further comprises at least one anchor tab positioned to facilitate attaching the lead anchor to a patient.

23. The patient therapy device of claim 21, wherein the anchor is positioned to engage the intermediate portion of the lead comprising the opening.

24. The patient therapy device of claim 20, wherein the anchor has a stiffness greater than a stiffness of the proximal portion of the lead.

25. The patient therapy device of claim 1, wherein the opening is a first opening and wherein the lead has a second opening disposed in the sidewall of the intermediate portion, the first opening being positioned between the second opening and the distal portion.

26. A spinal cord modulation lead for positioning within a patient and delivering electrical modulation signals to the patient at a treatment site, the lead comprising:
at least one electrical contact; and
a lead body having;
a proximal portion,
a distal portion, wherein the at least one electrical contact is disposed at the distal portion,
an intermediate portion disposed between the proximal portion and the distal portion,
a distal end, wherein the distal end is atraumatic,
a sidewall extending longitudinally along a longitudinal axis of the lead body, the sidewall having an opening at the intermediate portion, and
a lumen positioned interiorly from the sidewall and extending longitudinally between the distal end and the opening.

27. The lead of claim 26, wherein the opening is sized and shaped to receive a stylet removably insertable into the lumen through the opening.

28. The lead of claim 27, further comprising a membrane penetrable by the stylet and positioned over or within the opening.

29. The lead of claim 28, wherein the membrane includes a plug or a valve.

30. The lead of claim 29, wherein the valve includes a one-way valve.

31. The lead of claim 30, wherein the one-way valve includes a septum valve.

32. The lead of claim 26, wherein the distal portion is generally straight when positioned at the treatment site.

33. The lead of claim 26, wherein the lead has a lead length extending between a proximal end of the lead and the distal end.

34. The lead of claim 33, wherein the lead length is selected from the group consisting of about 50 centimeters (cm), about 55 cm, about 60 cm, about 65 cm, about 70 cm, about 75 cm, about 80 cm, about 85 cm, about 90 cm, about 95 cm, and about 100 cm.

35. The lead of claim 26, wherein the lead has a steerable length extending between the opening and the distal end of the lead.

36. The lead of claim 35, wherein the steerable length is selected from the group consisting of about 10 cm, about 15 cm, about 20 cm, about 25 cm, about 30 cm, about 35 cm, about 40 cm, about 45 cm, and about 50 cm.

37. The lead of claim 26, wherein the lead has a lead length selected from the group consisting of about 50 cm, about 60 cm, and about 70 cm, and the lead has a steerable length of about 30 cm.

38. The lead of claim 26, wherein the distal portion and the intermediate portion together have a first stiffness and the proximal portion has a second stiffness greater than the first stiffness.

39. The lead of any of claim 26, wherein the at least one contact is a first electrical contact and the opening is a first opening, and wherein the lead further comprises a second electrical contact at the proximal portion, and wherein the lead has a second opening in the sidewall, the second opening being between the first opening and a proximal end of the lead, with the lumen extending proximally from the second opening to the proximal end of the lead.

40. A method for treating a patient, comprising:
inserting a stylet into an opening within a sidewall of the lead, wherein the opening is located in an intermediate portion of the lead, between a distal end and a proximal end of the lead;
positioning the lead in a catheter, the lead carrying an electrode;
deploying the lead from the catheter; and
withdrawing the stylet from the lead through the opening by moving the stylet proximally away from the distal end of the lead through the lumen while the lead remains at a spinal modulation site.

41. The method of claim 40, wherein positioning the lead further comprises steering a steerable portion of the lead, the steerable portion comprising the intermediate portion and the distal end of the lead.

42. The method of claim 41, wherein deploying the lead further comprises:
moving the stylet into a lumen extending longitudinally between the opening and the distal end of the lead; and
positioning the lead with the stylet so that the lead is proximate to a spinal modulation site.

43. The method of claim 42, wherein positioning the lead further comprises moving the steerable portion of the lead relative to a proximal portion of the lead with the stylet.

44. The method of claim 40, further comprising preventing the stylet from extending outwardly from a lead body by positioning a lead anchor around a portion of the sidewall carrying the opening.

45. The method of claim 40, further comprising delivering electrical modulation signals to the spinal modulation site via the electrode carried by the lead.

46. The method of claim 40, further comprising positioning the stylet in the steerable portion of the lead before deploying the lead from the catheter.

47. A method for treating a patient, comprising:
withdrawing a stylet from a lead through an opening within a sidewall of the lead arranged at an intermediate portion of the lead;
inserting the stylet into the opening, wherein the intermediate portion is located between a proximal end and a distal end of the lead; and
inserting the stylet and the proximal end of the lead into a pulse generator.

48. The method of claim 47, wherein withdrawing the stylet includes moving the stylet proximally away from a distal end of the lead through a lead lumen while the lead remains at a modulation site.

49. The method of claim 47, further comprising:
inserting the stylet into the opening;
positioning the lead in a catheter, the lead carrying an electrode; and
deploying the lead from the catheter.

50. The method of claim 47, wherein the lead is an implantable lead.

51. The method of claim 50, wherein the implantable lead is a spinal cord stimulation lead, a deep brain stimulation lead, a peripheral nerve stimulation lead, or a sacral stimulation lead.

52. A patient therapy device, comprising:
a patient-implantable lead having a proximal portion, an intermediate portion and a distal portion, the intermediate portion having a sidewall, the sidewall having an opening, the lead further having at least one electrical contact disposed at at least one of the distal portion or the proximal portion, and a lumen inside of the lead, wherein the lumen extends longitudinally along a longitudinal axis of the lead between the opening and the at least one of the distal end or the proximal end, and is positioned off-center in the lead, when viewed in a cross-section normal to the longitudinal axis of the lead; and
a stylet having a shaft with a proximal region and a distal region, wherein the distal region of the stylet is sized and shaped to be removably inserted into the lumen through the opening.

* * * * *

UNITED STATES PATENT AND TRADEMARK OFFICE
CERTIFICATE OF CORRECTION

PATENT NO. : 11,420,045 B2
APPLICATION NO. : 16/367873
DATED : August 23, 2022
INVENTOR(S) : Pankaj Sunkeri et al.

It is certified that error appears in the above-identified patent and that said Letters Patent is hereby corrected as shown below:

On the Title Page

On the page 6, in Column 2, item (56) under "Other Publications", Line 1, delete "Intrel®" and insert -- Itrel --.

On the page 6, in Column 2, item (56) under "Other Publications", Line 10, delete "InterStrim" and insert -- InterStim --.

In the Specification

In Column 18, Line 31, delete "atraumatic" and insert -- atraumatic, --.

In the Claims

In Column 22, Line 50, in Claim 39, after "lead of" delete "any of".

Signed and Sealed this
Eighteenth Day of July, 2023

Katherine Kelly Vidal
*Director of the United States Patent and Trademark Office*